(12) United States Patent
Kivi et al.

(10) Patent No.: US 10,124,182 B2
(45) Date of Patent: Nov. 13, 2018

(54) MITIGATING IMPLANTABLE DEVICE POWER DRAIN ASSOCIATED WITH STALLED TELEMETRY SESSIONS

(71) Applicant: Medtronic, Inc., Minneapolis, MN (US)

(72) Inventors: Gary P. Kivi, Maple Grove, MN (US); Nicholas C. Wine, Minneapolis, MN (US); Matthew R. Yoder, Crystal, MN (US); Bo Zhang, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/471,308

(22) Filed: Mar. 28, 2017

(65) Prior Publication Data
US 2018/0243577 A1    Aug. 30, 2018

Related U.S. Application Data

(60) Provisional application No. 62/464,726, filed on Feb. 28, 2017.

(51) Int. Cl.
*G08B 23/00* (2006.01)
*A61N 1/39* (2006.01)
(Continued)

(52) U.S. Cl.
CPC .......... *A61N 1/3962* (2013.01); *A61B 5/0002* (2013.01); *A61B 5/0022* (2013.01);
(Continued)

(58) Field of Classification Search
CPC .... A61N 1/3962; A61N 1/36; A61N 1/36014; A61B 5/0002; A61B 5/0022;
(Continued)

(56) References Cited

U.S. PATENT DOCUMENTS

| 5,095,308 A | 3/1992 | Hewitt |
| 5,746,697 A * | 5/1998 | Swedlow ........... A61B 5/14551 600/323 |

(Continued)

FOREIGN PATENT DOCUMENTS

| WO | 03008013 A2 | 1/2003 |
| WO | 10087867 A1 | 8/2010 |
| WO | 11034468 A1 | 3/2011 |

OTHER PUBLICATIONS (PCT/US2018/019390) PCT Notification of Transmittal of the International Search Report and the Written Opinion of the International Searching Authority, dated May 28, 2018, 11 pages.

*Primary Examiner* — Zhen Y Wu

(57) ABSTRACT

Systems, apparatus, methods and computer-readable storage media that mitigate implantable medical device (IMD) power drain associated with stalled telemetry sessions are provided. In one embodiment, an IMD includes a housing configured to be implanted within a patient, a memory and a processor that executes executable components stored in the memory. The executable components include a communication component configured to receive a communication request from an external device via a telemetry communication link established between the IMD and the external device. The communication request can comprise a request for data. The executable components can also comprise a throughput monitoring component configured to monitor uplink throughput associated with transmission of the data by the IMD to the external device via the telemetry communication link based on reception of the communication request. The communication component is configured to terminate the telemetry communication link based on the uplink throughput being below a threshold value.

29 Claims, 10 Drawing Sheets

(51) Int. Cl.
  *H04L 12/26* (2006.01)
  *H04Q 9/02* (2006.01)
  *A61B 5/00* (2006.01)
  *A61N 1/36* (2006.01)
  *H04W 76/30* (2018.01)

(52) U.S. Cl.
  CPC .............. *A61B 5/6801* (2013.01); *A61N 1/36* (2013.01); *A61N 1/36014* (2013.01); *H04L 43/0888* (2013.01); *H04L 43/16* (2013.01); *H04Q 9/02* (2013.01); *H04W 76/30* (2018.02); *H04Q 2209/43* (2013.01)

(58) Field of Classification Search
  CPC ... A61B 5/6801; H04L 43/0888; H04L 43/16; H04Q 9/02; H04Q 2209/43; H04W 76/06
  USPC ...................................... 340/870.02
  See application file for complete search history.

(56) References Cited

U.S. PATENT DOCUMENTS

| | | | | |
|---|---|---|---|---|
| 5,924,979 | A * | 7/1999 | Swedlow | A61B 5/14551 600/300 |
| 6,002,671 | A * | 12/1999 | Kahkoska | H04M 3/304 348/192 |
| 6,200,265 | B1 * | 3/2001 | Walsh | A61B 5/0031 128/903 |
| 6,480,476 | B1 * | 11/2002 | Willars | H04B 1/1615 370/311 |
| 7,653,017 | B2 | 1/2010 | Huylebroeck | |
| 7,656,853 | B2 | 2/2010 | Albulet | |
| 7,899,401 | B2 * | 3/2011 | Tanaka | H04B 17/345 340/10.1 |
| 7,987,378 | B2 | 7/2011 | Lee et al. | |
| 7,999,655 | B2 * | 8/2011 | Yoshikawa | B60R 25/04 340/5.72 |
| 8,172,766 | B1 * | 5/2012 | Kayyali | A61B 5/02055 128/204.23 |
| 8,386,051 | B2 | 2/2013 | Rys | |
| 8,412,964 | B2 | 4/2013 | Lee et al. | |
| 8,428,528 | B2 * | 4/2013 | Sutton | H04B 1/40 340/10.1 |
| 8,475,372 | B2 | 7/2013 | Schell et al. | |
| 8,959,368 | B2 | 2/2015 | Lee et al. | |
| 9,072,914 | B2 | 7/2015 | Greenhut et al. | |
| 9,445,051 | B1 * | 9/2016 | Muthsandra Kantharaju | H04N 7/15 |
| 9,687,658 | B2 | 6/2017 | Wu et al. | |
| 9,855,433 | B2 | 1/2018 | Shahandeh et al. | |
| 9,894,691 | B1 | 2/2018 | Hellman | |
| 2002/0123672 | A1 * | 9/2002 | Christopherson | A61N 1/37282 600/300 |
| 2003/0171791 | A1 * | 9/2003 | KenKnight | A61N 1/36514 607/60 |
| 2003/0229383 | A1 * | 12/2003 | Whitehurst | A61N 1/372 607/60 |
| 2004/0006492 | A1 * | 1/2004 | Watanabe | A61B 5/0002 705/2 |
| 2004/0113771 | A1 * | 6/2004 | Ozaki | A61B 5/0002 340/539.12 |
| 2005/0283208 | A1 * | 12/2005 | Von Arx | A61N 1/37223 607/60 |
| 2006/0128308 | A1 | 6/2006 | Michael et al. | |
| 2008/0161660 | A1 * | 7/2008 | Arneson | A61B 1/00016 600/302 |
| 2008/0167531 | A1 * | 7/2008 | McDermott | A61B 5/0031 600/300 |
| 2008/0232405 | A1 * | 9/2008 | Gallo | H04L 47/10 370/498 |
| 2008/0262573 | A1 * | 10/2008 | Seeberger | A61N 1/37223 607/60 |
| 2009/0216100 | A1 * | 8/2009 | Ebner | A61B 5/0002 600/347 |
| 2009/0264964 | A1 * | 10/2009 | Abrahamson | A61N 1/37252 607/60 |
| 2010/0315225 | A1 * | 12/2010 | Teague | A61B 5/0024 340/539.12 |
| 2012/0044810 | A1 * | 2/2012 | Koto | H04W 72/1252 370/237 |
| 2012/0108922 | A1 | 5/2012 | Schell et al. | |
| 2012/0172690 | A1 | 7/2012 | Anderson et al. | |
| 2012/0172941 | A1 | 7/2012 | Rys | |
| 2012/0182917 | A1 * | 7/2012 | Edlund | A61N 1/37276 370/311 |
| 2012/0215286 | A1 * | 8/2012 | Rahman | A61N 1/37276 607/60 |
| 2012/0271902 | A1 * | 10/2012 | Baliga | H04L 43/0811 709/209 |
| 2012/0313760 | A1 * | 12/2012 | Okano | G06F 19/3418 340/10.1 |
| 2013/0079836 | A1 * | 3/2013 | Srivastava | A61N 1/37235 607/4 |
| 2013/0109989 | A1 * | 5/2013 | Busse | A61B 5/1102 600/527 |
| 2013/0214909 | A1 | 8/2013 | Meijers et al. | |
| 2014/0188348 | A1 | 7/2014 | Gautama et al. | |
| 2014/0214104 | A1 | 7/2014 | Greenhut et al. | |
| 2014/0330327 | A1 | 11/2014 | Thompson-Nauman et al. | |
| 2015/0133951 | A1 | 5/2015 | Seifert et al. | |
| 2015/0265843 | A1 * | 9/2015 | Wu | A61N 1/37252 607/60 |
| 2015/0341785 | A1 | 11/2015 | Young et al. | |
| 2016/0007873 | A1 * | 1/2016 | Huelskamp | A61B 5/0452 600/510 |
| 2017/0026777 | A1 | 1/2017 | Denboer et al. | |
| 2018/0021589 | A1 | 1/2018 | Wu et al. | |

\* cited by examiner

MITIGATING IMPLANTABLE DEVICE POWER DRAIN ASSOCIATED WITH STALLED TELEMETRY SESSIONS

RELATED APPLICATIONS

This application claims the benefit of the filing date of a U.S. Provisional Application Ser. No. 62/464,726, filed Feb. 28, 2017, which is incorporated herein in its entirety.

TECHNICAL FIELD

This disclosure relates generally to implantable devices and, more particularly, to systems, apparatus, methods and computer-readable storage media that facilitate mitigating implantable device power drain associated with stalled telemetry sessions.

BACKGROUND

Modern healthcare facilitates the ability for patients to lead healthy and full lives. Implantable medical devices (IMDs) are often utilized for such medical advances. For example, IMDs such as pacemakers, implantable cardioverter-defibrillators (ICDs), cardiac re-synchronization therapy (CRT) devices, neurostimulators, and drug pumps can facilitate management with a wide range of ailments, including, but not limited to, cardiac arrhythmias, diabetes, and Parkinson's disease.

The sophistication of IMDs is evolving to provide for advanced computing and telemetry capabilities. The latest IMDs support delivery of telemetry for remote monitoring and programming over various-range, high-bandwidth wireless links, and emerging devices will communicate with other interoperating IMDs. For example, many modern IMDs are configured to be responsive to on-demand telemetry communication requests from external devices after implantation. These requests generally prompt the IMD to establish a telemetry connection with the external device to allow the external device to read data collected from the IMD, to program the IMD, or to control operation of the IMD. After the external device has received the requested data or otherwise successfully completed programming of the IMD, the external device and the IMD can disable the telemetry connection to reduce power consumption associated with maintaining the connection and render the IMD available for establishing a new telemetry connection with the external device or another external device.

There are a number of scenarios that can slow data communication between an IMD and external device after establishing a telemetry connection. For example, after an IMD and an external device have established a telemetry connection, either device may not be able to transmit or receive data from the other due to interference, movement of the respective devices out of transmission range, or a development error. However, even though little or no data is successfully communicated in these scenarios, the respective devices maintain the connection, resulting in a waste of power and preventing the IMD from establishing another potentially viable connection. Accordingly, systems, apparatus, methods and computer-readable storage media that minimize maintenance of stalled telemetry connections with external devices are desired.

SUMMARY

The following presents a simplified summary of one or more of the embodiments in order to provide a basic understanding of one or more of the embodiments. This summary is not an extensive overview of the embodiments described herein. It is intended to neither identify key or critical elements of the embodiments nor delineate any scope of embodiments or the claims. Its sole purpose is to present some concepts of the embodiments in a simplified form as a prelude to the more detailed description that is presented later. It will also be appreciated that the detailed description can include additional or alternative embodiments beyond those described in the Summary section.

Embodiments described herein include systems, apparatus, methods and computer-readable storage media that facilitate mitigating implantable device power drain associated with stalled telemetry sessions. In some embodiments, the implantable device is or includes an IMD. In other embodiments, the implantable device is or includes a device configured to interact with the IMD. In these embodiments, both the implantable device and the IMD can be implanted within a patient.

In one embodiment, an IMD is provided. The IMD is configured to be at least partially implanted within a patient and includes a housing configured to be implanted at least partially within the patient. The IMD can also include a memory, within the housing, that stores executable components, and circuitry, within the housing, and configured to at least one of obtain sensed physiological data associated with the patient or deliver a therapy to the patient. The IMD also includes a processor, within the housing, that executes the executable components stored in the memory. The executable components include at least a communication component configured to receive a communication request from an external device via a telemetry communication link established between the IMD and the external device, wherein the communication request comprises a request for data from the IMD. The executable components further include a throughput monitoring component configured to monitor uplink throughput associated with transmission of the data by the IMD to the external device via the telemetry communication link based on reception of the communication request, wherein the communication component is further configured to terminate the telemetry communication link based on the uplink throughput being below a threshold value.

In one or more implementations, the throughput monitoring component is configured to determine the uplink throughput based on a number of application data packets comprising the data that are successfully transmitted by the IMD to the external device via the telemetry communication link per connection interval. In another implementation, the throughput monitoring component is configured to determine the uplink throughput based on time delays between successful transmissions of data packets comprising the data by the IMD to the external device via the telemetry communication link. In some implementations, the threshold value varies based on a type of the data. In other implementations, the data comprises a first type of data and the uplink throughput comprises first uplink throughput, and wherein the throughput monitoring component is configured to monitor the first uplink throughput independently from second uplink throughput associated with transmission of a second type of data by the IMD to the external device via the telemetry communication link. In yet another implementation, the communication component is further configured to terminate the telemetry communication link based on the uplink throughput being below the threshold value for a defined period of time following reception of the communication request. With this implementation, the defined period of time can vary based on a type of telemetry session associated with the communication request.

In another embodiment, a device external to an IMD is described that includes, a memory that stores executable components, and a processor that executes the executable components stored in the memory. These executable components can comprise a communication component configured to transmit data to the IMD via a telemetry communication link established between the device and the IMD, and a throughput monitoring component configured to monitor uplink throughput associated with transmission of the data by the device to the IMD, wherein the communication component is further configured to terminate the telemetry communication link based on the uplink throughput being below a threshold value. In one implementation, the throughput monitoring component is configured to determine the uplink throughput based on number of application data packets comprising the data that are transmitted by the device per connection interval. In another implementation, the throughput monitoring component is configured to determine the uplink throughput based on time delays between successful transmissions of data packets comprising the data by the device.

In another embodiment, a method of communicating by an IMD configured to at least one of obtain sensed physiological data associated with a patient or deliver a therapy to the patient, is provided. The method can include receiving, by an IMD comprising a processor, a data request from an external device via a telemetry communication link established between the implantable medical device and the external device, wherein the data request comprises a request for data from the implantable medical device. The method can further include monitoring, by the implantable medical device, uplink throughput associated with transmission of the data by the implantable medical device to the external device via the telemetry communication link based on reception of the data request, and terminating, by the implantable medical device, the telemetry communication link based on the uplink throughput being below a threshold value. In one implementation, the monitoring the uplink throughput comprises determining the uplink throughput based on number of application data packets comprising the data that are successfully transmitted by the implantable medical device per connection interval. In another implementation, the monitoring the uplink throughput comprises determining the uplink throughput based on time delays between successful transmissions of data packets comprising the data by the implantable medical device. In some implementations, threshold value varies based on a type of the data. Further, in some implementations, the monitoring comprises monitoring the uplink throughput associated with the transmission of the data based on a type of the data.

Still in another embodiment, a system is disclosed that comprises an external device, and an implantable medical device configured to be at least partially implanted within a patient. The IMD comprises a first memory that stores first executable components, and a first processor that executes the first executable components stored in the first memory. In one or more implementations, the first executable components comprise a first communication component configured to establish a secure telemetry connection with the external device based on reception of a connection data request from the external device. The first executable components can further comprises a first throughput monitoring component configured to monitor first uplink throughput associated with transmission of first data by the implantable medical device to the external device via the secure telemetry connection, and wherein the first communication component is further configured to terminate the secure telemetry connection based on a first determination, by the first throughput monitoring component, that the first uplink throughput is below a threshold value. In some embodiments, the external device comprises a second memory that stores second executable components, and a second processor that executes the second executable components stored in the second memory. With these implementations, the second executable components comprise a second throughput monitoring component configured to monitor second uplink throughput associated with transmission of second data by the external device to the implantable medical device via the secure telemetry connection. The second executable components further comprise a second communication component configured to terminate the secure telemetry connection based on a second determination, by the second throughput monitoring component, that the second uplink throughput is below the threshold value.

Other embodiments and various non-limiting examples, scenarios and implementations are described in more detail below. The following description and the drawings set forth certain illustrative embodiments of the specification. These embodiments are indicative, however, of but a few of the various ways in which the principles of the specification can be employed. Other advantages and novel features of the embodiments described will become apparent from the following detailed description of the specification when considered in conjunction with the drawings.

DETAILED DESCRIPTION

The following detailed description is merely illustrative and is not intended to limit embodiments and/or application or uses of embodiments. Furthermore, there is no intention to be bound by any expressed or implied information presented in the preceding Technical Field, Background or Summary sections, or in the Detailed Description section.

One or more embodiments are now described with reference to the drawings, wherein like referenced numerals are used to refer to like elements throughput. In the following description, for purposes of explanation, numerous specific details are set forth in order to provide a more thorough understanding of the one or more embodiments. It is evident, however, in various cases, that the one or more embodiments can be practiced without these specific details.

Additionally, the following description refers to components being "connected" and/or "coupled" to one another. As used herein, unless expressly stated otherwise, the terms "connected" and/or "coupled" mean that one component is directly or indirectly connected to another component, mechanically, electrically, wirelessly, inductively or otherwise. Thus, although the figures may depict example arrangements of components, additional and/or intervening components may be present in one or more embodiments.

Figure 1:
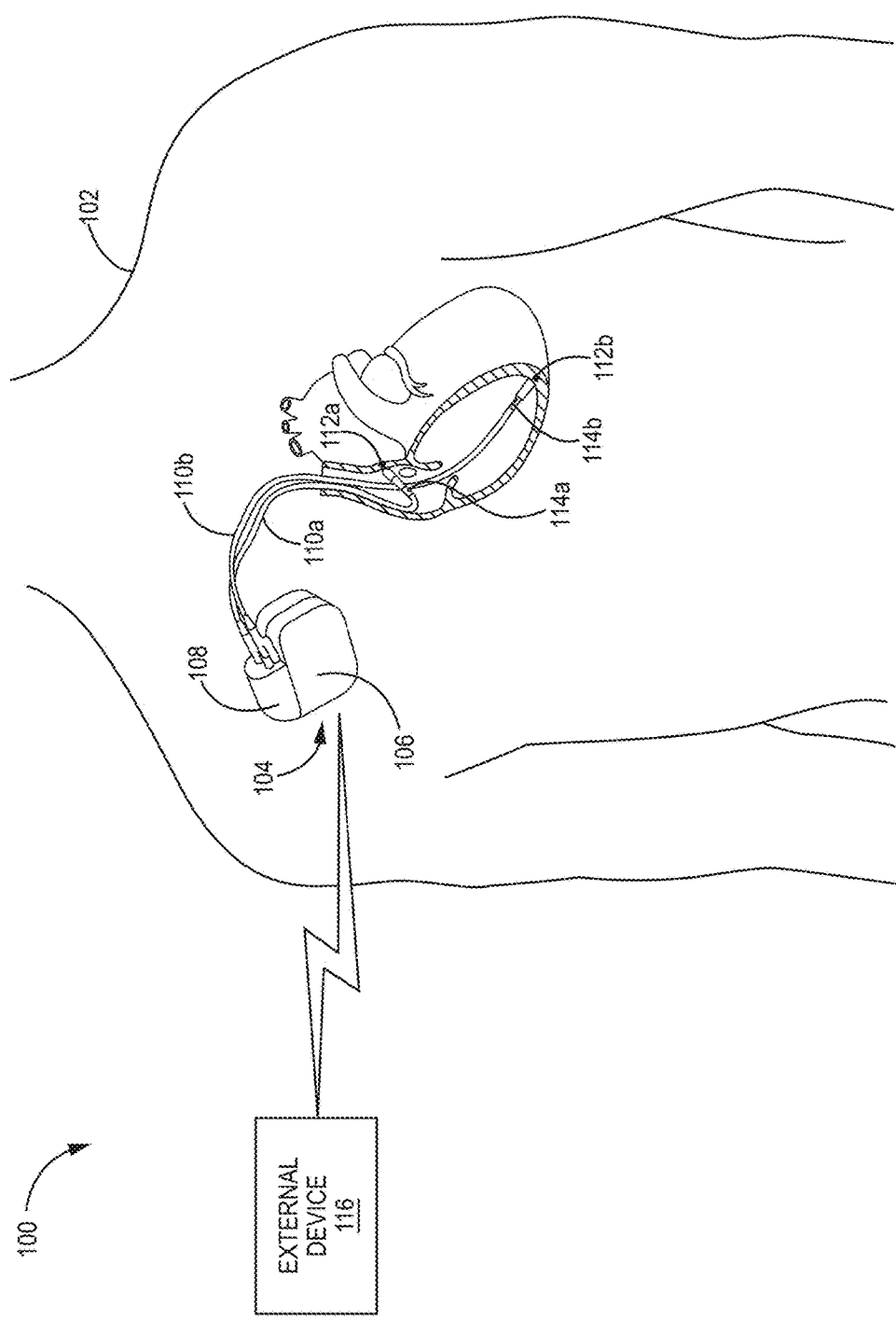
FIG. 1 illustrates a schematic diagram of example, non-limiting medical device telemetry systems configured to facilitate mitigating implantable device power drain associated with stalled telemetry sessions in accordance with one or more embodiments described herein.

With reference now to the drawings, FIG. 1 illustrates a schematic diagram of an example, non-limiting medical device telemetry system 100 configured to facilitate mitigating implantable device power drain associated with stalled telemetry sessions in accordance with one or more embodiments described herein. In the embodiment shown, medical device telemetry system 100 includes an implantable device 104 implanted within a body 102, and an external device 116. In some embodiments, the implantable device 104 is an IMD that is also configured to facilitate one or more diagnostic or treatment functions relative to the body 102. In other embodiments, the implantable device 104 is separate from an IMD (not shown in this embodiment) that is also implanted within the body 102 and communicatively and/or electrically coupled to the IMD.

Embodiments of devices, apparatus and systems herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

One or more embodiments of medical device telemetry system 100 are described in connection with mitigating power drain by an implantable device 104 associated with stalled telemetry sessions between the implantable device 104 and an external device 116. In particular, the implantable device 104 can be configured to use telemetry to exchange various types of information with external devices, including external device 116. For example, in some implementations, the implantable device 104 is an IMD configured to sense physiological data or biometric data from the body 102. In another implementation, the IMD can be configured to provide therapy to the body 102 and retain the therapy information regarding the therapy that was provided. In other implementations, the implantable device 104 can be coupled to an IMD configured to sense the physiological or biometric data or provide the therapy to the body 102. With these implementations, the implantable device 104 can be configured to transmit information to the external device 116 regarding sensed physiological or biometric data captured by the implantable device from the body 102. The implantable device 104 can also be configured to transmit information to the external device 116 regarding diagnostic determinations made based on the sensed physiological or biometric data. In another example, the implantable device 104 can be configured to transmit therapy information to the external device 116 regarding a therapy delivered to the body. In other embodiments, the implantable device 104 can be configured to transmit performance information to the external device 116 regarding operation or performance of the implantable device 104 (e.g., power level information, configuration information, information regarding monitored telemetry session statistics, etc.).

The external device 116 can also be configured to send information to the implantable device 104 using telemetry. For example, the external device 116 can be configured to send the implantable device interrogation requests that direct the implantable device 104 to send the external device 116 requested data, such as data stored in memory of the implantable device 104 or data captured or measured by the implantable device in real-time (e.g., electrogram data or other physiological or biometric data sensed by the implantable device 104). In another example, the external device 1116 can be configured to send the implantable device 104 control information or control signals that facilitate programming or re-programming the implantable device 104. For instance, in an implementation in which the implantable device 104 is configured to apply a drug or therapy to the body 102, the external device 116 can send the implantable device 104 control information that configures the particular drug or therapy delivery schedule or dosage by the implantable device 104. In another example, the external device 116 can be configured to use telemetry to send the implantable device 104 configuration information that controls various communication modes of the implantable device 104.

In some embodiments, the external device 116 can also provide information received from the implantable device 104 (or determinations or inferences made at the external device 116 based on the information) to a remote server device (not shown) via one or more wired or wireless networks. By way of example, but not limitation, the remote server device can be associated with a networked medical monitoring service that is configured to remotely monitor information collected by implantable devices worn by patients (e.g., implantable device 104). The remote server device can monitor and log the data, process the data and/or provide other users (e.g., medical caregiver personnel) access to the data via one or more networks (not shown). For example, the one or more networks can include a cellular network, a wide area network (WAD, e.g., the Internet), a local area network (LAN), or a personal area network (PAN). For example, an external device 116 can communicate with the remote server device (and vice versa) using virtually any desired wired or wireless technology, including, for example, cellular, WAN, wireless fidelity (Wi-Fi), Wi-Max, WLAN, and etc. In some embodiments, the remote server device can also notify one or more user devices in response to reception of information that indicates a trigger event. For example, the remote server device can notify a patient device (e.g., a device associated with the person wearing the implantable device 104) and/or a caregiver device in response to reception of physiological information indicating the patient's heart electrical activity is abnormal. In another example, the remote server device can notify a patient device and/or the caregiver device in response to reception of information indicating telemetry connectivity between the implantable device 104 and the external device 116 is or may be compromised. In some embodiments, as described infra, the remote server device can also facilitate trusted pairing between an external device (e.g., external device 116) and an implantable device (e.g., implantable device 104).

The implantable device 104 can be configured to perform telemetry with a variety of external devices. For example, the external device 116 can include, but is not limited to, a desktop computer, a laptop computer, a television, an Internet enabled television, a mobile phone, a smartphone, a tablet personal computer (PC), a personal digital assistant PDA, a heads-up display (HUD), virtual reality (VR) headset, augmented reality (AR) headset, or another type of wearable computing device. In some embodiments, the external device 116 includes a PC that is associated with the user wearing the implantable device 104. For example, the external device 116 can include a smartphone or other type of handheld or wearable device that is owned and operated by the patient wearing the implantable device 104. In another example, the external device 116 can include a PC that is operated by a medical caregiver of the patient, such as the patient's physician, nurse, at-home caregiver, mother, etc. In yet another example, the external device 116 can include a dedicated and/or stationary electronic computing device designed to remain at a home of the patient or at an office of a physician.

In various exemplary embodiments, the external device 116 includes an off-the-shelf device purchased at a store that can be configured to perform a variety of computing applications. These devices are configured to employ various types of non-proprietary telemetry protocols to communicate with other devices. For example, communication devices such as implantable device 104 and external device 116 have to agree on many physical layer and link layer aspects of the data to be exchanged before a successful connection can be established. Rules defining how to establish a connection and perform telemetry communications are referred to in wireless communication technology as "protocols." Communication protocols cover authentication, error detection and correction, and signaling. Communications protocols are implemented in hardware and software. The term "non-proprietary telemetry communication technology or protocol" refers to any standardized telemetry communication technology or protocol that can be commercially used by more than one entity, either in an open source or licensed context. Many non-proprietary telemetry communication technologies/protocols have publically available specifications. Many modern mobile devices such as smart phones, tablet PCs and the like are configured to communicate using various non-proprietary telemetry protocols including but not limited to, BLUETOOTH®, BLUETOOTH® low energy (BLE), near field communication (NFC), Wireless Fidelity (Wi-Fi) protocol, Zigbee®, RF4CE, WirelessHART, 6LoWPAN, Z-Wave, ANT, and the like. In various embodiments, the implantable device 104 and/or the external device 116 can be configured to communicate using one or more non-proprietary telemetry protocols, including but not limited to the aforementioned non-proprietary telemetry communication protocols (e.g., BLUETOOTH®, BLE, etc.). In some embodiments, the implantable device 104 and/or the external device 116 can also be configured to communicate using one or more proprietary telemetry protocols.

Regardless of the particular telemetry communication protocol employed by the implantable device 104 and the external device 116 to communicate, in accordance with the embodiments described herein, the respective devices first establish a telemetry "connection" in order to communicate. In telecommunication and computing in general, a "connection" is the successful completion of necessary arrangements so that two or more entities (e.g., devices, applications, users of the devices or application, etc.) can communicate. Two devices can establish a telemetry connection using a telemetry link. A "link" refers to a communications channel that connects two or more communicating devices. This link may be an actual physical link or it may be a logical link that uses one or more actual physical links. In some implementations, in which two devices are connect using wireless communications (e.g., telemetry), the link between the respective devices is a logical link. Thus in various embodiments described herein, the terms "connection" and "link" are used interchangeably.

In accordance with one or more embodiments, the implantable device 104 can be configured to be establish a telemetry connection with an external device (e.g., external device 116) based on reception of a connection request from the external device. The connection request can generally prompt the implantable device 104 to establish a telemetry connection with the external device to allow the external device to read data collected from the implantable device 104 and/or to program or control operation of the implantable device 104. In some embodiments, the connection request can specify or indicate a specific type of telemetry session to be performed between the implantable device 104 and the external device. For example, the specific type of telemetry session can relate to a purpose of the telemetry session, a type of data that is to be exchanged between the respective devices, a duration of the telemetry session, a signaling flow for the telemetry session, or another defined variable characteristic of the telemetry session.

The particular, signal flow for setting up and establishing the telemetry connection can vary depending on the telemetry protocol employed. In some embodiments, in order for the implantable device 104 and the external device 116 to communicate sensitive information between one another (e.g., physiological information sensed by the implantable device 104, programming information controlling operation of the implantable device, etc.), the implantable device 104 and the external device must establish and employ a "secure" telemetry connection or link. A "secure" telemetry connection or link is a connection or link that is encrypted by one or more security protocols to ensure the security of data flowing between two or more nodes. For example, according to various non-proprietary telemetry protocols (e.g., BLUETOOTH®, BLE, and the like), in order to initiate a telemetry session with the implantable device 104, the external device 116 can send a connection request to the implantable device 104 requesting to establish a telemetry connection with the implantable device. Upon reception of a connection request from an external device 116, an initial telemetry connection can be established between the implantable device 104 and the external device 116. The implantable device 104 can then determine whether the external device 116 is authorized to communicate with the implantable device 104 prior to establishing a secure telemetry connection with the external device 116.

In accordance with various non-proprietary telemetry communication protocols (e.g., BLUETOOTH®, BLE), in order to establish a secure telemetry connection between devices (e.g., between the implantable device 104 and the external device 116), the devices perform a pairing process that establishes a secure, trusted relationship between the devices. The pairing process is a mechanism where the parties involved in the communication exchange their identity information to set up trust and get the encryption information needed for the future data exchange. The secure, trusted relationship ensures that both devices have authorized telemetry communication between the respective devices and often involves a user/device authorization and/or identity verification procedure. After two devices have established a secure, trusted relationship (also referred to as becoming "paired"), the respective devices can communicate with one another without a subsequent authorization procedure. For example, in accordance with various embodiments, after the implantable device 104 has paired with an external device (e.g., external device 116), the external device can establish a secure telemetry connection with the implantable device 104 by sending a connection request with information that identifies the external device. The implantable device 104 can then accept the connection request based on a determination that the external device has been previously paired with the implantable device 104. The respective devices can further communicate data between one another using the encryption keys previously established between the devices in the pairing process.

After the implantable device 104 and the external device establish a telemetry connection, or in some embodiments, a secure telemetry connection, the respective devices can maintain the connection to carry out a telemetry session. In telecommunications, a telemetry "session" refers to a series of interactions between two communication end points (e.g., the implantable device 104 and the external device 116) that occur during the span of a single telemetry connection. The session begins when the connection is established at both ends and terminates when the connection is ended. For instance, depending on the purpose of the telemetry session, the external device 116 can send the implantable device 104 requests for certain data, such as data stored in memory of the implantable device 104 or data collected or sensed by the implantable device in real-time. Such requests for data are referred to herein as "interrogation requests." The implantable device 104 can be configured to respond to an interrogation request by sending the external device 116 the requested data. In another example, the external device 116 can send the implantable device 104 programming commands and the implantable device 104 can receive and apply the programming commands. In accordance with some telemetry communication protocols, each time a device (e.g., the implantable device 104 or the external device 116) receives downlink data from the other device (e.g., external device 116 or the implantable device), during a telemetry session, the device can be configured to send an acknowledgment message to the other device that informs the other device regarding reception of the downlink data.

After the external device has received all requested data and/or otherwise successfully completed programming of the implantable device 104, the respective devices can disable the telemetry connection to reduce power consumption associated with maintaining the connection and render the implantable device 104 available for establishing a new telemetry connection with the external device or another external device. For example, in accordance with various proprietary and non-proprietary telemetry communication protocols, maintenance of a telemetry connection between two devices (e.g., the implantable device 104 and the external device 116) consumes a significant amount of device power. For example, in various embodiments in which the implantable device 104 has an established a telemetry connection with an external device, the implantable device 104 can be configured to operate in a highly responsive state by maintaining activation of a receiver or transceiver of the implantable device 104. During a telemetry session, the implantable device 104 can also be configured to activate its receiver or transceiver to regularly transmit data to the external device. In addition, in accordance with some telemetry communication protocols, the implantable device 104 can be configured to only have a single telemetry connection established with a single external device at a time.

There are a number of things that can slow data communication between an implantable device (e.g., implantable device 104) and external device (e.g., external device 116) after establishing a telemetry connection. For example, after the implantable device 104 and the external device 116 have established a telemetry connection, either device may not successfully be able to transmit or receive data from the other due to interference, movement of the respective devices out of transmission range, a development error or another type of error. However, even though little or no data is successfully communicated in these scenarios, the respective devices can be configured to maintain the connection, resulting in a waste of power and preventing the implantable device from establishing another potentially viable connection. In addition, in accordance with some telemetry communication protocol, upon successful completion of a telemetry session, in order for the external device 116 or the implantable device 104 to end the telemetry session, one or both devices can be configured to send an "end session," or "disable connection," request to the other device requesting to end or otherwise disable the telemetry connection. Either device can be configured to maintain the connection unless the "end session," or "disable connection," request is received. In some implementations, due to interference, movement of the respective devices out of transmission range, a development error or another type of error, either device may not receive the "end session," or "disable connection," request, and thus maintain the connection even though no data is communicated between the respective devices, again resulting in a waste of power and preventing either device from establishing another potentially viable connection. In another example, the external device may simply fail to send the "end session" or "disable connection" to the implantable device 104. For instance, this can happen if a patient in which the implantable device 104 is implanted is hospitalized and a clinician operating the external device 116 forgets to press the end session button upon completion of a successful interrogate session. It can also occur if an external device 116 that serves as a remote monitor malfunctions and does not close the telemetry session. For example, such a malfunction could involve an application of the external device 116 being stuck in a frozen or hung condition that prevented it from closing the session.

In accordance with various embodiments of the subject disclosure, telemetry connections characterized by slow or no data communication between two communication devices due to interference, movement of the respective devices out of transmission range, a development error, another type of error or a failure for either device to receive an "end session" or "disable connection" request, and the like, are referred to herein as "stalled telemetry sessions." Likewise, when a telemetry session between two communication devices is characterized by a defined period of slow or no data communication, the telemetry session is considered to be "stalled." In this regard, "no data communication" can include failure for either device to successfully transmit data to the other device for a defined period of time, wherein successful transmission means the transmitted data was received by the other device. The data can include any type of data (e.g., control data, authorization data, application data, memory data, waveform data, etc.) or a defined type of data. However, in various exemplary embodiments, the type of data that is monitored is application data packets (e.g., as opposed to merely link layer data packets). The defined period of time can vary. For example, in some embodiments, the defined period of time can be about 10 seconds. In other embodiments, the defined period of time can be about 30 minutes. In some implementations, "slow data communication" can include failure for either device to successfully transmit a minimum amount of data to the other device for a defined period time. The data can include any type of data or a defined type of data. The defined period of time can vary. In other implementations, "slow data communication" can include can include failure for either device to successfully transmit data to the other device at a minimum rate or frequency for a defined period time. The data can include any type of data (e.g., control data, authorization data, packet data, etc.) or a defined type of data. The defined period of time can vary.

In view of these scenarios, the subject disclosure provides mechanisms for mitigating device power drain associated with maintaining stalled telemetry sessions. In one or more embodiments, the implantable device 104 and/or the external device 116 can be configured to detect occurrence of a stalled telemetry session based on uplink throughput associated with the telemetry session. Based on determination that a current telemetry session between the implantable device 104 and the external device has stalled, the implantable device 104 and/or the external device can be configured to automatically disable the telemetry connection and end the telemetry session. For example, in one implementation, the implantable device 104 can be configured to monitor uplink throughput associated with data transmitted by the implantable device 104 to the external device 116 during a telemetry session. The implantable device 104 can further determine if and when the uplink throughput falls below a predefined threshold amount or level. Based on the uplink throughput being below the predefined threshold amount or level, the implantable device 104 can be configured to disable the telemetry connection established between the implantable device and the external device 116. In another implementation, the external device 116 can be configured to monitor uplink throughput associated with data transmitted by the external device 116 to the implantable device 104 during a telemetry session. The external device 116 can further determine if and when the uplink throughput falls below a predefined threshold amount or level. Based on the uplink throughput being below the predefined threshold amount or level, the external device 116 can be configured to disable the telemetry connection established between the external device 116 and the implantable device 104. Additional details of example embodiments of the subject techniques for detecting and disabling stalled telemetry sessions between an implantable device 104 and an external device 116 are discussed below with respect to FIGS. 2-8.

It is to be appreciated that the implantable device 104 can include one or more devices, transducers and/or circuits that can facilitate telemetry communication and disablement of telemetry communication. For example, the implantable device 104 can include a transmitter that transforms electrical power into a signal associated with transmitted data packets. Additionally, the implantable device 104 can include one or more devices, transducers and/or circuits that can facilitate receiving information from one or more devices (e.g., the external device 116, a server, etc.). For example, the implantable device 104 can include a receiver that transforms a signal into electrical power.

In the example shown in medical device telemetry system 100, a person operating the external device 116 is a patient in which the implantable device 104 is implanted. In another example, another person (e.g., such as medical caregiver) interacting with the patient in which the implantable device 104 is implanted can operate the external device 116 outside the body 102 in which the implantable device 104 is located. In various embodiments, the implantable device 104 can include any number of different types of implantable devices configured to communicate with the external device 116 or another external device. The particular, size, shape, placement and/or function of the implantable device 104 may not be critical to the subject disclosure in some embodiments.

In one embodiment, as mentioned, the implantable device 104 is or includes an IMD. For example, some example IMDs can include, but are not limited to, cardiac pacemakers, cardiac defibrillators, cardiac re-synchronization devices, cardiac monitoring devices, cardiac pressure monitoring devices, spinal stimulation devices, neural stimulation devices, gastric stimulation devices, diabetes pumps, drug delivery devices, and/or any other medical devices. In various embodiments, however, the implantable device 104 can be or include any number of other types of implantable devices that are not IMDs.

For exemplary purposes, the implantable device 104 is illustrated in medical device telemetry system 100 as an IMD implanted within the chest of a patient and configured to provide medical treatment or therapy associated with a heart disease or condition (e.g., an implantable cardioverter-defibrillator (ICD) and/or a pacemaker). In addition to the medical treatment, the implantable device 104 can also be configured to provide the data packetizing and communication operations described herein. The implantable device 104 includes a housing 106 within which electrical components and one or more power sources are housed. The electrical components can be powered via the one or more power sources. A power source (not shown) can include, but is not limited to, a battery, a capacitor, a charge pump, a mechanically derived power source (e.g., microelectromechanical systems (MEMs) device), or an induction component. The various embodiments described herein can provide improved management of power associated with the one or more power sources.

The electrical components can vary depending on the particular features and functionality of the implantable device 104. In various embodiments, these electrical component can include, but are not limited to, one or more processors, memories, transmitters, receivers, transceivers, sensors, sensing circuitry, therapy circuitry, antennas and other components. In an embodiment, the electrical components can be formed on or within a substrate that is placed inside the housing 106. The housing 106 can be formed from conductive materials, non-conductive materials or a combination thereof. For example, housing 106 can include a conductive material, such as metal or metal alloy, a non-conductive material such as glass, plastic, ceramic, etc., or a combination of conductive and non-conductive materials. In some embodiments, the housing 106 can be a biocompatible housing (e.g., a liquid crystal polymer, etc.).

In the embodiment shown, the implantable device 104 is also an IMD and further includes leads 110a,b connected to the housing 106. The leads 110a,b extend into the heart and respectively include one or more electrodes. For example, as depicted in medical device telemetry system 100, leads 110a,b each include a respective tip electrodes 112a,b and ring electrodes 114a,b located near a distal end of their respective leads 110a,b. When implanted, tip electrodes 112a,b and/or ring electrodes 114a,b are placed relative to or in a selected tissue, muscle, nerve or other location within the body 102 of the patient. As depicted in medical device telemetry system 100, tip electrodes 112a,b are extendable helically shaped electrodes to facilitate fixation of the distal end of leads 110a,b to the target location within the body 102 of the patient. In this manner, tip electrodes 112a,b are formed to define a fixation mechanism. In other embodiments, one or both of tip electrodes 112a,b may be formed to define fixation mechanisms of other structures. In other instances, leads 110a,b may include a fixation mechanism separate from tip electrodes 112a,b. Fixation mechanisms can be any appropriate type, including a grapple mechanism, a helical or screw mechanism, a drug-coated connection mechanism in which the drug serves to reduce infection and/or swelling of the tissue, or other attachment mechanism.

Leads 110a,b are connected at a proximal end of the implantable device 104 via connector block 108. Connector block 108 may include one or more receptacles that interconnect with one or more connector terminals located on the proximal end of leads 110a,b. Leads 110a,b are ultimately electrically connected to one or more of the electrical components within housing 106. One or more conductors (not shown) extend within leads 110a,b from connector block 108 along the length of the lead to engage the ring electrodes 114a,b and tip electrodes 112a,b, respectively. In this manner, each of tip electrodes 112a,b and ring electrodes 114a,b is electrically coupled to a respective conductor within its associated lead bodies. For example, a first electrical conductor can extend along the length of the body of lead 110a from connector block 108 and electrically couple to tip electrode 112a and a second electrical conductor can extend along the length of the body of lead 110a from connector block 108 and electrically couple to ring electrode 114a. The respective conductors may electrically couple to circuitry, such as a therapy module or a sensing module, of the implantable device 104 via connections in connector block 108. In one or more embodiments, the implantable device 104 is configured to deliver therapy to the heart (or other location) via the electrical conductors to one or more of electrodes 112a and 112b and 114a and 114b. In the case of pacing therapy, for example, therapy circuitry within the implantable device 104 can generate and deliver pacing pulses via a unipolar electrode configuration, e.g., using electrodes 112a and 112b and a housing electrode of the implantable device 104. In other instances, the therapy circuitry within the implantable device 104 can deliver pacing pulses via a bipolar electrode configuration, e.g., using electrodes 112a and 112b and ring electrodes 114a and 114b. The therapy circuitry may include one or more pulse generators, capacitors, and/or other components capable of generating and/or storing energy to deliver as pacing therapy in accordance with a pacing regime stored within memory.

Implantable device 104 can also receive sensed electrical signals on the electrical conductors from one or more of electrodes 112a and 112b and 114a and 114b. The implantable device 104 can sense the electrical signals using either a unipolar or bipolar electrode configuration. Sensing circuitry of the implantable device 104 may process the sensed electrical signals and the implantable device 104 may analyze the processed and/or or sensed electrical signals and provide the pacing as a function of the sensed electrical signal. The sensing circuitry may include one or more sense amplifiers, filters, rectifiers, threshold detectors, comparators, analog-to-digital converters (ADCs), or other analog or digital components.

The configuration, features and functionality of implantable device 104 are merely provided as an example. In other examples, the implantable device 104 can include more or fewer leads extending from the housing 106. For example, the implantable device 104 can be coupled to three leads, e.g., a third lead implanted within a left ventricle of the heart of the patient. In another example, the implantable device 104 can be coupled to a single lead that is implanted within the ventricle of the heart of the patient. In other embodiments, the lead may be an extravascular lead with the electrodes implanted subcutaneously above the ribcage/sternum or substernally underneath or below the sternum. Example extravascular ICDs having subcutaneous electrodes are described in U.S. Patent Publication No. 2014/0214104 (now U.S. Pat. No. 9,072,914) (Greenhut et al.) and U.S. Patent Publication No. 2015/0133951 (Seifert et al.), each of which is incorporated herein in its entirety. One example extravascular ICD having substernal electrodes is described in U.S. Patent Publication No. 2014/0330327 (Thompson-Nauman et al.). In some embodiments, the implantable device 104 can include other leads (e.g., atrial lead and/or left ventricular lead). As such, implantable device 104 can be used for single chamber or multi-chamber cardiac rhythm management therapy. In addition to more or fewer leads, each of the leads may include more or fewer electrodes. In instances in which the implantable device 104 is used for therapy other than pacing (e.g., defibrillation or cardioversion), the leads can include elongated electrodes, which may, in some instances take the form of a coil. The therapy circuitry of the implantable device 104 can generate and deliver defibrillation or cardioversion shocks to the heart via any combination of the elongated electrodes and housing electrode. The therapy circuitry may include one or more high voltage (HV) output capacitors and a HV charging circuit, which may include one or more capacitors, resistors, inductors, transformers, switches, or other analog or digital components, and discharging circuitry to deliver cardioversion or defibrillation therapy, including, for example, an H-bridge circuit. In another embodiment, the implantable device 104 can include leads with a plurality of ring electrodes (e.g., as used in some implantable neurostimulators), without a tip electrode or with one of the ring electrodes functioning as the "tip electrode."

In another embodiment, the implantable device 104 may include no leads, as in the case of an intracardiac pacemaker or a leadless pressure sensor. In the case of an intracardiac pacemaker, the device may include a housing sized to fit wholly within the patient's heart. In one example, the housing may have a volume that is less than 1.5 cc and, more preferably, less than 1.0 cubic centimeter (cc). However, the housing may be greater than or equal to 1.5 cc in other examples. The intracardiac pacemaker includes at least two electrodes spaced apart along the outer portion of the housing for sensing cardiac electrogram signals and/or delivering pacing pulses. Example intracardiac pacemakers are described in commonly-assigned U.S. Patent Publication No. 2012/0172690 (Anderson et al.), U.S. Patent Publication No. 2012/0172941 (now U.S. Pat. No. 8,386,051) (Kenneth), and U.S. Patent Publication No. 2014/0214104 (now U.S. Pat. No. 9,072,914) (Greenhut et al.), each of which is incorporated herein in its entirety. In the case of a leadless pressure sensor, the device can include a housing having a fixation member and a pressure sensing component. One example of a leadless pressure sensor is described in U.S. Patent Publication No. 2012/0108922 (now U.S. Pat. No. 8,475,372) (Schell et al.), which is incorporated herein in its entirety.

Figure 2:
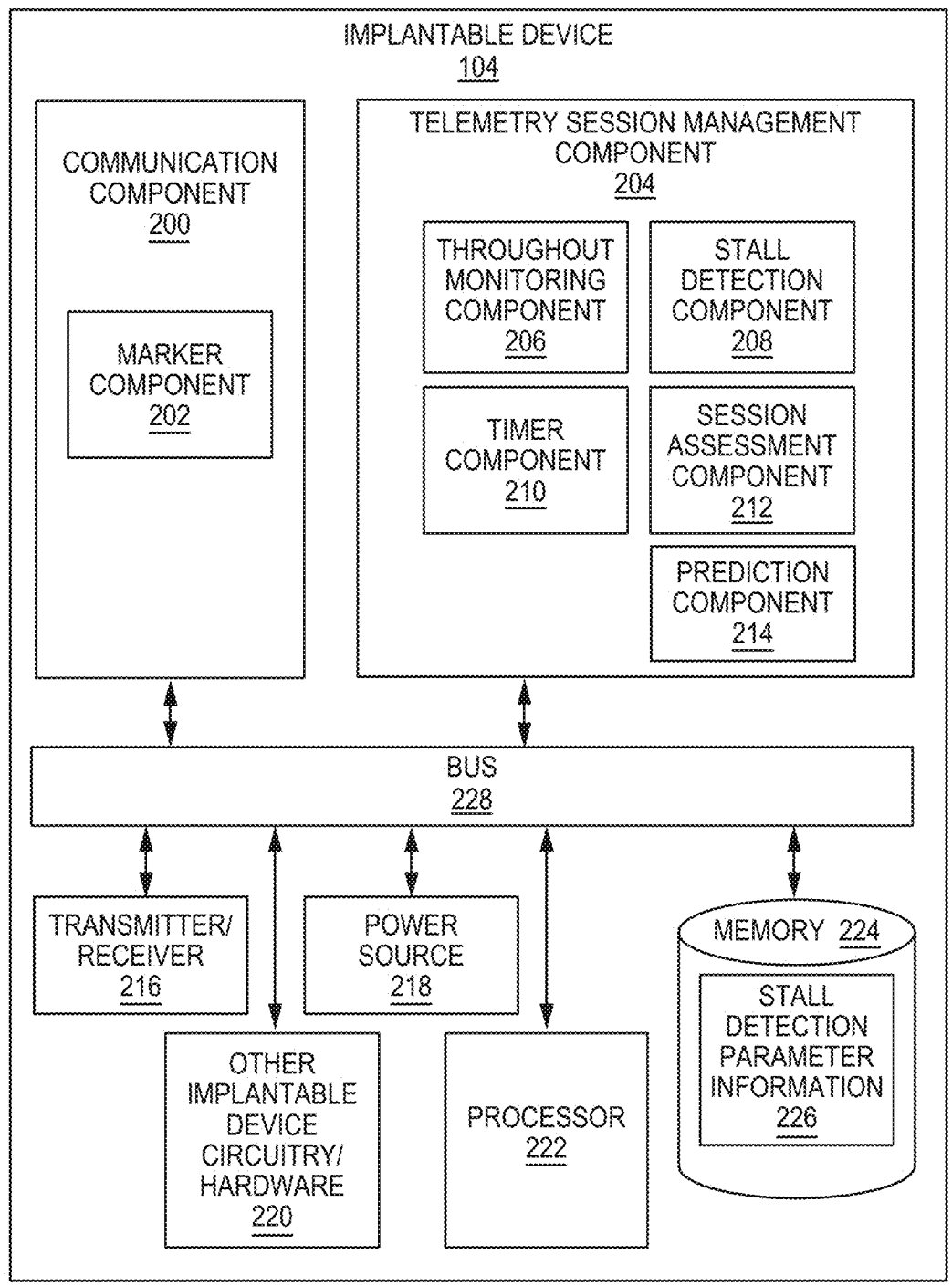
FIG. 2 illustrates a block diagram of an example, non-limiting implantable device in accordance with one or more embodiments described herein.

FIG. 2 illustrates a block diagram of an example, non-limiting implantable device (e.g., implantable device 104) in accordance with one or more embodiments described herein. The implantable device 104 can include a communication component 200 to facilitate performing telemetry sessions with external devices (e.g., external device 116) and a telemetry session management component 204 to facilitate managing performance of the telemetry sessions by the communication component. The implantable device 104 can also includes a transmitter/receiver 216 (or transceiver), a power source 218, and other implantable device circuitry/hardware 220.

Various aspects of the device, systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. Accordingly, in one or more embodiments, the implantable device 104 can include memory 224 configured to store computer executable components and instructions (e.g., communication component 200 and the telemetry session management component 204). The implantable device 104 can also include a processor 222 to facilitate operation of the instructions (e.g., computer executable components and instructions) by the implantable device 104. Implantable device 104 can include a bus 228 that couples the various components of the implantable device 104, including, but not limited to, the communication component 200, the telemetry session management component 204, the transmitter/receiver 216, the power source 218, the other implantable device circuitry/hardware 220, the processor 222 and the memory 224. Repetitive description of like elements employed in other embodiments described herein is omitted for sake of brevity.

With reference to FIGS. 1 and 2, the communication component 200 is configured to facilitate telemetry communication between implantable device 104 and one or more external devices (e.g., external device 116). The communication component 200 can include software, hardware, or a combination of software and hardware that is configured to facilitate telemetry performance by the implantable device 104. For example, the communication component 200 can be configured to control operation of the transmitter/receiver 216 (or transceiver) to facilitate establishing a telemetry connection or link with the external device 116 and to control transmission and reception of data packets by the implantable device 104. In accordance with various embodiments described herein, the communication component 200 can be configured to receive connection requests from external devices, set up or establish a telemetry connection with an external device (and in some embodiment secure telemetry connection), conduct a telemetry session with the external device via the telemetry connection, and terminate the telemetry session.

The communication component 200 can be configured to facilitate telemetry communication between the implantable device 104 and an external device (e.g., external device 116) using a variety of telemetry communication protocols including proprietary and non-proprietary telemetry protocols. For example, in one or more embodiments, communication component 200 can communicate with external device 116 using NFC, or another type of communication protocol over a PAN or a LAN (e.g., a Wi-Fi network) that can provide for communication over greater distances than NFC protocol or that can provide various advantages (such as increased security). In some embodiments, the communication component 200 can control transmission and reception of data packets via a communication channel associated with a communication protocol utilizing lower energy consumption than a conventional communication protocol for wirelessly transmitting data. For example, in a non-limiting example, communication component 200 controls transmission and reception of data packets using BLE protocol. Other communication protocols that can be employed by communication component 200 to communicate with external device 116 can include, but are not limited to, other BLUETOOTH® communication protocols, a Session Initiation Protocol (SIP) based protocol, a Zigbee® protocol, a RF4CE protocol, a WirelessHART protocol, a 6LoWPAN (IPv6 over Low power Wireless Personal Area Networks) protocol, a Z-Wave protocol, an ANT protocol, an ultra-wideband (UWB) standard protocol, a cellular communications protocol (e.g., second, third, fourth and fifth Generation Partnership Project (GGP) protocols, Long Term Evolution (LTE), protocols), machine type communication (MTC) protocols, Narrowband Internet-of-things (NB-IoT) protocols, other radio frequency (RF) communication protocols, non-RF communication protocols (e.g., induction based, optical based, audio based, etc.) and/or other proprietary and non-proprietary communication protocols.

The type of the transmitter/receiver 216 can vary depending on the type of telemetry protocol the implantable device 104 is configured to employ. In some embodiments, the transmitter/receiver 216 can be configured to perform different types of telemetry protocols (e.g., BLUETOOTH®, BLE, NFC, Wi-Fi, Zigbee®, etc.). In other embodiments, the implantable device 104 can include a plurality of different transmitters/receivers that are respectively configured to perform different types of telemetry communication protocols. In some embodiments, rather than including a transmitter and a receiver that do not share common circuitry, the implantable device 104 can include a transceiver.

The telemetry session management component 204 can be configured to facilitate managing one or more aspects of a telemetry session between the implantable device 104 and an external device (e.g., external device 116). The telemetry session management component 204 can include throughput monitoring component 206, stall detection component 208, timer component 210, session assessment component 212, and prediction component 214. In accordance with various embodiments of the subject disclosure, the telemetry session management component 204 can be particularly configured to manage detecting and terminating stalled telemetry sessions between the implantable device 104 and an external device 116 based on uplink throughput associated with data transmitted by the implantable device 104 to the external device 116 (e.g., via communication component 200) during the telemetry session.

The throughput monitoring component 206 can be configured to monitor uplink throughput associated with transmission (or lack thereof) of data by the implantable device 104 to the external device during a telemetry session. Throughput is the rate of successful message delivery over a communication channel. Throughput is usually measured in bits per second (bit/s or bps), and sometimes in data packets per second or data packets per time slot. Accordingly, uplink throughput relates to how quickly data packets are transmitted and how many data packets are transmitted. Likewise, downlink throughput relates to to how quickly data packets are received and how many data packets are received. There are many elements that affect throughput over a communication channel, including the maximum theoretical channel capacity or bandwidth, which varies based on the particular telemetry protocol employed, and various other factors that have an effect on the maximum theoretical channel capacity (e.g., limitations of underlying analog physical medium, available processing power of the system components, and end-user behavior).

For example, with respect to BLE, there are many elements that affect/limit BLE's throughput such as the connection interval (e.g., how often the devices talk), number of packets per connection interval, packet length, and time delays between packets, and overhead bytes in a packet such as packet length, data integrity check, and general packet information. In some embodiments, a BLE connection can include only two devices, where one is a central device (which would be the external device 116 in most implementations) and the other device is a subordinate device (which would be the implantable device 104 in most implementations). Each side communicates with the other on a given period called "connection interval." According to the BLE specification, the minimum connection interval can be set to about 7.5 milliseconds and increases in steps of 1.25 milliseconds up to 4.0 seconds. A BLE telemetry session can thus consist of several connection intervals. Each instance of communication between two devices during a connection interval is called a communication event. When initiating a communication event, the central or master (e.g., the external device), specifies the connection interval. With BLE, more than two packets can be communicated in a single connection event. The maximum number of packets per connection event is dependent on the BLE stack/chipsets. The theoretical maximum application data throughput in BLE can be described as the following formula:

Throughput=Packets per second×Data per packet

In one or more embodiments, after the implantable device 104 has established a telemetry connection (or in some embodiments, a secure telemetry connection), with an external device 116, the throughput monitoring component 206 can be configured to begin monitoring uplink throughput associated with data transmitted (or not transmitted) by the implantable device 104 to the external device during the telemetry session. For example, the throughput monitoring component 206 can continually determine the uplink throughput over the course of the telemetry session (e.g., every N milliseconds or seconds). As discussed above, various factors can affect the uplink throughput. In some embodiments, the throughput monitoring component 206 can be configured to determine the uplink throughput based on a number of application data packets successfully transmitted by the implantable device 104 (e.g., via communication component 200) to the external device per connection interval. In another embodiment, the throughput monitoring component 206 can be configured to determine the uplink throughput based on a number of data packets successfully transmitted by the implantable device 104 (e.g., via communication component 200) to the external device every M seconds (e.g., 5 seconds, 10 seconds, etc.). The throughput monitoring component 206 can also determine the uplink throughput based on an amount of data per packet. In some implementations, the external device 116 can be configured to send the implantable device 104 an acknowledgement message each time it receives a data transmission from the implantable device 104. With these implementations, data transmission by the implantable device 104 to the external device 116 can be considered successful based on reception of an acknowledgment message for that data transmission.

Thus in some embodiments, the throughput monitoring component 206 can be configured to determine the uplink throughput based on reception of acknowledgment messages acknowledging successful transmission of data packets by the implantable device 104. The throughput monitoring component 206 can also be configured to determine the uplink throughput based on timing of reception of acknowledgment messages acknowledging successful transmission of data packets by the implantable device 104.

In other embodiments, the throughput monitoring component 206 can be configured to determine the uplink throughput based on time delays between successful transmissions of data packets by the implantable device 104 to the external device 116. For example, the throughput monitoring component 206 can determine the uplink throughput as a function of average duration of time between successful transmissions of data packets.

The telemetry session management component 204 can include timer component 210 to track the progression of time during a telemetry session. For example, the timer component 210 can track the duration of the telemetry session beginning at the point of establishment of the telemetry connection. The timer component 210 can also track occurrence of communication events and duration of time between communication events. For example, the timer component 210 can track timing of unsuccessful data transmissions (wherein an acknowledgment message was expected but not received), timing of successful data transmissions (wherein an acknowledgment message was expected and received), timing between transmission successful data transmissions, timing of reception of acknowledgment messages, timing of reception of other downlinks, and the like. In another example, the timer component 210 can track duration of time between reception of an interrogation request and successful transmission of a response to the interrogation request.

The stall detection component 208 can regularly or continuously evaluate the session uplink throughput as determined by the throughput monitoring component 206. The stall detection component 208 can further determine if a telemetry session has "stalled" based on the monitored uplink throughput. In this sense, the stall detection component 208 can detect a lack of progress in a telemetry session based on no or low uplink data transmissions successfully performed by the implantable device 104. In one implementation, the stall detection component 208 can be configured to detect or determine that a telemetry session has stalled if the uplink throughput falls below a defined threshold amount or level. For example, if the throughput monitoring component 206 determines that the telemetry session throughput is X bps and X is less than or equal to the threshold value of Y bps, then stall detection component 208 can determine that the telemetry session has stalled. In another implementation, the stall detection component 208 can be configured to detect or determine that a telemetry session has stalled if the uplink throughput falls below a defined threshold amount or level for a predefined duration, referred to herein as the "stall period." For example, if the throughput monitoring component 206 determines that the telemetry session throughput is X bps or less for more than the stall period of Z seconds or minutes and X is less than or equal to the threshold value of Y, then stall detection component 208 can determine that the telemetry session has stalled. The threshold values or levels for the minimum uplink throughput (e.g., Y) and the stall period duration (Z), can be predefined and stored in memory 224 of the implantable device 104. For example, in the embodiment shown, the memory 224 can include a data structure or cell that includes stall detection parameter information 226. The stall detection parameter information 226 can include information or rules that define how the throughput monitoring component 206 should measure uplink throughput (e.g., number data of successful data packets per millisecond or second, timing or reception of acknowledgment messages, timing between successful transmission of data packets, etc.), and how the stall detection component 208 should determine whether a telemetry stall has occurred (e.g., the threshold amount for minimal uplink throughput and/or duration or time for which the uplink throughput can be less than the threshold amount).

In another implementation, in which the throughput monitoring component 206 is configured to monitor average duration of time between successful transmissions of data packets, the stall detection component 208 can be configured to determine that a telemetry session has stalled based on the average duration of time being below a threshold level. In yet another implementation, in which the throughput monitoring component 206 is configured to monitor duration of time between successful transmissions of data packets, the stall detection component 208 can determine the telemetry session has stalled based on a pattern in the duration of time between successful transmissions of data packets that indicates a session stall. For example, the stall detection component 208 can be configured to detect a stalled telemetry session based on a significant drop (e.g., with respect to a threshold degree of deviation) in successful data transmissions by the implantable device.

Based on detection of a stall event, the stall detection component 208 can be configured to direct the communication component 200 to disable or terminate the telemetry connection. For example, in response to detection of the uplink throughput being below a defined threshold amount or being below a defined threshold amount for a maximum stall period, the stall detection component 208 can direct the communication component 200 to terminate the telemetry connection between the implantable device 104 and the external device 116. The communication component 200 can be configured to respond accordingly by terminating or otherwise disabling the telemetry connection between the implantable device 104 and the external device 116. For example, in one implementation, the communication component 200 can disable the telemetry connection by switching to operating in a communication mode wherein the implantable device 104 is not connected to the external device yet responsive to receiving new connection requests. Accordingly, the implantable device 104 can become available for establishing a new and potentially viable telemetry connection with the external device or another external device. In another implementation, the communication component 200 can disable the telemetry connection by temporarily turning off the transmitter/receiver 216. For example, in embodiments in which the implantable device 104 is configured to employ a BLUETOOTH® technology, the communication component 200 can temporarily turn off the BLUETOOTH® functionality of the implantable device 104.

In some embodiments, the telemetry session management component 204 can employ different criteria for detecting stalled telemetry sessions based on the type of telemetry session being performed between the implantable device 104 and the external device 116. The type of a telemetry session can relate to a type of data that is communicated between the implantable device 104 and the external device 116 during the telemetry session as well as a manner in which the type of data is communicated. For example, the implantable device 104 can be configured to perform different types of telemetry sessions with external devices, such as read-only sessions, read and program sessions, read and control sessions, program only sessions, and the like. In another example, the type of the telemetry session can be characterized by the type of data that is authorized for communication between the implantable device 104 and the particular external device 116. For example, a telemetry session that is used to communicate highly sensitive information between the implantable device 104 and an external device 116 can be considered a first type of telemetry session while a telemetry session that is used to communicate less sensitive information between the implantable device 104 and an external device 116 can be considered a second type of telemetry session. In another example, the type of the telemetry session can be characterized by the level of authority or data access that is authorized for communication between the implantable device 104 and the particular external device 116. With these examples, the type of the telemetry session can be based on the particular external device with which the implantable device is communicating and a defined authority or access level associated with that device (e.g., as defined in memory 224 of the implantable device 104).

In another example, the type of telemetry session can be characterized by the purpose of the telemetry session, such as for remote monitoring or clinical use. For example, in some implementations, an external device 116 can establish a telemetry session with the implantable device 104 for the purpose of monitoring physiological information associated with the body 102 that is captured by the implantable device or for monitoring other information associated with operation of the implantable device 104. Monitoring sessions are generally characterized by short durations (e.g., a few minutes or less) and involve sending, by the external device 116 to the implantable device 104, of information stored in memory of the implantable device 104 in response to reception of an interrogation request for the information from the external device 116 for the information. The information received by the external device 116 from the implantable device 104 in association with a monitoring session can be processed to facilitate monitoring the health of the patient over time.

On the contrary, a clinician telemetry session is generally employed to facilitate more invasive and on-demand or real-time communication between the implantable device 104 and an external device operated by a doctor or clinician of a patient wearing the implantable device 104. For example, a clinician telemetry session can be employed during interaction between the patient and the patient's doctor or clinician, such as during scheduled office visits, during routine check-ups, during emergency situations, and the like. Using an external device (e.g., external device 116) the doctor or clinician can establish a clinician session with the implantable device 104 to program or re-program an operating parameter of the implantable device 104, command the implantable device 104 to apply a therapy to the body, send the external device specific data captured by the implantable device 104 in real-time, send the remote clinician device specific data associated with the implantable device 104 that is only authorized for clinician use, and the like. In some implementations, a clinician session is used to receive waveform data captured by the implantable device 104. For example, in an embodiment in which the implantable device is an ICD, the ICD can be configured to capture electrical signals of the heart via one or more leads (e.g., leads 110*a,b*), referred to herein as waveform data. With these implementations, during a clinician session, the external device 116 can send the implantable device a request for waveform data. In response to reception of the requested, the implantable device can respond by continually transmitting the external device waveform data in real-time (e.g., as it is captured) while the patient is interacting with the clinician operating the remote clinician device. Clinician telemetry sessions can last substantially longer than monitoring sessions (e.g., from several minutes to an hour or longer) and can be characterized by varying degrees of data exchange between the external device 116 and the implantable device 104.

According to these embodiments, the specific stall detection criteria used by the stall detection component 208 to determine whether a session has stalled can vary based on the type of the telemetry session and/or the type of data that is communicated between the implantable device 104 and the external device. In various implementations, the session assessment component 212 can be configured to evaluate a connection request and/or other data received from the external device in association with a telemetry session to determine a type of the telemetry session. The type of the telemetry session can further control the specific stall detection criteria (e.g., uplink throughput minimum thresholds, stall periods, thresholds/requirements for time delays between transmissions, etc.) employed by the stall detection component 208 to determine if and when the telemetry session has stalled. Information associating different defined types of telemetry sessions and the specific stall detection criteria can further be stored in memory 224 (e.g., as stall detection parameter information 226).

In some implementations, the external device 116 can provide the implantable device 104 with information identifying the type or the telemetry session (e.g., in the connection request or in another transmission following the connection requests). For example, the external device 116 can provide the implantable device 104 with information that identifies the telemetry session as a read-only session, a read program session, a read and control session, a monitoring session, a clinician session or another type of session. In another implementation, the external device 116 can provide the implantable device 104 with information from which the session assessment component 212 can discern the type of the telemetry session (e.g., in the connection request or in another transmission following the connection requests). For example, this information can include an identifier for the external device, a type of data requested in an interrogation request, a type of command provided by the external device, and the like. With these implementations, the implantable device 104 can include information stored in memory 224 that the session assessment component 212 can used to facilitate determining the type of a telemetry session based on information provided by the external device. For example, the implantable device 104 can store information in memory 224 that associates an identifier for an external device with a type of telemetry session the external device is authorized to perform. In another example, the implantable device 104 can store information that associates a particular request for a particular type of data with a particular type of telemetry session.

The stall detection component 208 can further select the appropriate stall detection parameter information (e.g., uplink throughput minimum threshold and stall period, minimum average duration between successful transmission of data packets, etc.) to apply for evaluating the uplink throughput based on the type of the telemetry session, as determined by the session assessment component 212. For example, as discussed above, the nature of a monitoring telemetry session is generally shorter (e.g., a few minutes or less) and involves relatively non-invasive data communications relative to a clinician session (e.g., which can be up to an hour or longer and can involve programming or remote control of the implantable device 104). According to this example, in some implementations, the stall period for a monitoring session can be significantly lower (e.g., 10 seconds) relative to the stall period for a clinician session (e.g., 30 minutes). In another example, a first type of telemetry session can be characterized by requiring the implantable device 104 to transmit data packet to the external device at a much higher frequency relative to a second type of telemetry session. With this example, the minimum uplink throughput threshold for the first type of telemetry session can be higher than the minimum uplink throughput threshold for the second type of telemetry session.

In one or more additional embodiments, the telemetry session management component 204 can also be configured to evaluate uplink throughput for purposes of detecting stall events based on the type of data that is transmitted. For example, in some scenarios, the implantable device 104 can be configured to transmit the external device different types of data during a telemetry session. For instance, as described above, during a clinician session, the implantable device 104 can respond to a request for waveform data and begin transmitting the waveform data to the external device 116 over the course of the clinician session. During the same clinician session, the external device 116 can send the implantable device 104 an interrogation request for information stored in memory of the implantable device 104, send the implantable device control commands, or otherwise perform telemetry communications with the implantable device 104 in addition to the waveform data communications. According to this example, the implantable device 104 can be configured to transmit the waveform data using one-way communications and transmit other data associated with the interrogation requests or the control commands data using two way communications. One-way communications include data transmissions that do not prompt the receiving device to send an acknowledgment message while two-way data communications prompt the receiving device to send an acknowledgment message. Thus with one-way data communications, the communication component 200 does not receive confirmation whether the data transmission was successfully received.

According to these embodiments, for purposes of determining whether a telemetry session has stalled, the throughput monitoring component 206 may be more concerned with uplink throughput associated with a first type of data (e.g., two-way communication data, data read from memory of the implantable device 104, data transmissions responsive to control or programming commands sent by the external device, etc.) relative to second type of data (e.g., one-way communication data, waveform data, etc.). Thus in some implementations, the throughput monitoring component 206 can be can be configured to selectively monitor uplink throughput associated with different types of data that is transmitted by the implantable device 104 to the external device 116. For example, in one implementation, the throughput monitoring component 206 can be configured to only monitor uplink throughput associated with a first type of data and ignore uplink throughput associated with a second, third, fourth, etc. type of data. In another example, the throughput monitoring component 206 can be configured to independently monitor uplink throughput associated with transmission of a two or more different types of data by the implantable device. For purposes of detecting a stall event, the stall detection component 208 can further be configured to independently evaluate uplink throughput associated with the different types of data. For example, in one implementation, the stall detection component 208 can be configured to ignore uplink throughput associated with a second type of data (e.g., waveform data) and only evaluate uplink throughput associated with a first type of data (e.g., data read from memory). In another implementation, the stall detection component 208 can be configured to analyze total uplink throughput associated with a combination of transmission of two or more different types of data. However, the when evaluating the total uplink throughput, the stall detection component 208 can be configured to employ a function that weights uplink throughput associated with the different types of data differently. For example, the function can apply a more stringent minimum uplink throughput threshold and stall period for a first type of data (e.g., two-way communication data) relative to a second type of data (e.g., waveform data). In example, the function can apply less value to uplink throughput associated with the second type of data relative to the first type of data.

In some embodiments, the telemetry session management component 204 can also include prediction component 214 to facilitate predicting stall events based on the monitored uplink throughput information. In particular, the prediction component 214 can be configured to identify characteristics of the monitored uplink throughput information that indicate the onset of a possible stall event. The prediction component 214 can further facilitate initiating remedial action by the communication component 200 to prevent the possible stall event or minimize harm associated with occurrence of the stall event. In some implementations, the prediction component 214 can be configured to recognize defined characteristics of the monitored throughput data that have been previously determined to be associated with the onset of a stalled telemetry session. For example, the defined characteristics can include a sharp drop in uplink throughput, a sharp drop in uplink throughput following transmission or reception of a particular type of data, a sharp drop in uplink throughput after the implantable device received a request for defined information, and the like. In this regard, the threshold of change in uplink throughput that corresponds to a sharp drop can be defined. In another example, the defined characteristics can include a pattern in the monitored uplink throughput data that indicates the onset of degradation in quality of the telemetry session.

In some implementations, the prediction component 214 can employ machine learning techniques to facilitate the prediction of a stall event. For example, the prediction component 214 can evaluate recorded information for past stall events, including the uplink throughput information monitored for past stall events. Using machine learning techniques, the prediction component 214 can identify one or more distinguishing characteristics in the uplink throughput information that are associated with an onset of as stall event.

Based on detection of one or more defined characteristic that indicate a possible stall event may occur, the prediction component 214 can further facilitate initiating remedial action by the communication component 200 to prevent the possible stall event or minimize harm associated with occurrence of the stall event. For example the prediction component 214 can notify the communication component 200 that a possible stall event has been predicted. In one implementation, based on the notification, the communication component 200 can be configured to prioritize the transmission of data to the external device 116 such that data considered more critical than other data is communicated first. According to this implementation, the communication component 200 can access information stored in memory 224 that identifies a priority classification associated with different types of data and transmit data having a higher priority classification before transmission of data having a lower priority classification.

In another implementation, based on prediction of an onset of a stall event, the communication component 200 can be configured to send the external device 116 a warning message that informs the external device 116 regarding the degradation of uplink throughput. For example, the warning message can inform the external device 116 that uplink throughput is low. If the warning message is received by the external device 116, the external device 116 can further be configured to generate a prompt that can be presented to a user of the external device 116 based on reception of the warning message. For example, the prompt can inform the user of the external device 116 that uplink throughput is low. Based on reception of the prompt, the user of the external device 116 can take action to facilitate improving the uplink throughput, such as moving the external device 116 closer to the implantable device 104, or moving the external device 116 and the implantable device 104 (e.g., by moving the patient in which the implantable device 104 is implanted) to an area that is associated with less interference.

In another implementation, based on detection of a possible stall event by the prediction component 214, the communication component 200 can be configured to backup critical information associated with the telemetry session. For example, the communication component 200 can make copies of critical data that is queued for transmission to the external device 116. In some embodiments, the communication component 200 can also include marker component 202 to place markers where data transmission was terminated in response to a determination that a stall event has occurred (e.g., by the stall detection component 208). For example, the marker component 202 can be configured to generate information that identifies data that was attempting to be transmitted to the external device 116 and/or was queued for transmission to the external device 116 at the point when the telemetry session stalled. This maker information can further be stored in memory 224. Accordingly, if the telemetry session is reinitiated, the communication component 200 can access the marker information and begin transmitting data to the external device 116 at the point where the telemetry session was terminated.

The implantable device 104 can further include a suitable power source 218 to drive the functionality of implantable device 104 and to provide power to the various electrical components of the implantable device 104. In one or more embodiments, the power source 218 includes but is not limited to, a battery, a capacitor, a charge pump, a mechanically derived power source (e.g., microelectromechanical systems (MEMs) device), or an induction component. The various embodiments described herein can provide improved management of power associated with the power source 218. For example, the mechanism of terminating stalled telemetry session minimizes unnecessary and excessive usage of the power source 218 associated with maintaining a telemetry connection (e.g., associated with prolonged receiver and/or transmitter activation), thereby increasing the lifespan of the implantable device 104.

The implantable device 104 can also include various other implantable device circuitry/hardware 220 to facilitate operation of the various components of the implantable device 104. For example, the other implantable device circuitry/hardware 220 can include, but is not limited to: a pulse generator, capacitors, leads (e.g., leads 110*a,b*), electrodes (e.g., tip electrodes 112*a,b* and ring electrodes 114*a,b*), sensors, accelerometers, pumping mechanisms, reservoirs, communication component 200 related hardware (e.g., antennas, transmitters, receivers, transceivers repeaters, etc.), a therapy output module, and the like. The other implantable device circuitry/hardware 220 can facilitate various operations of the implantable device, including, but not limited to, medical related operations (e.g., sensing electrical signals of the heart, dispensing a drug, etc.), and telemetry communication mode operations of the implantable device (e.g., RF telemetry and non-RF telemetry such as induction, optical based, audio based, vibration based, etc.).

Figure 3:
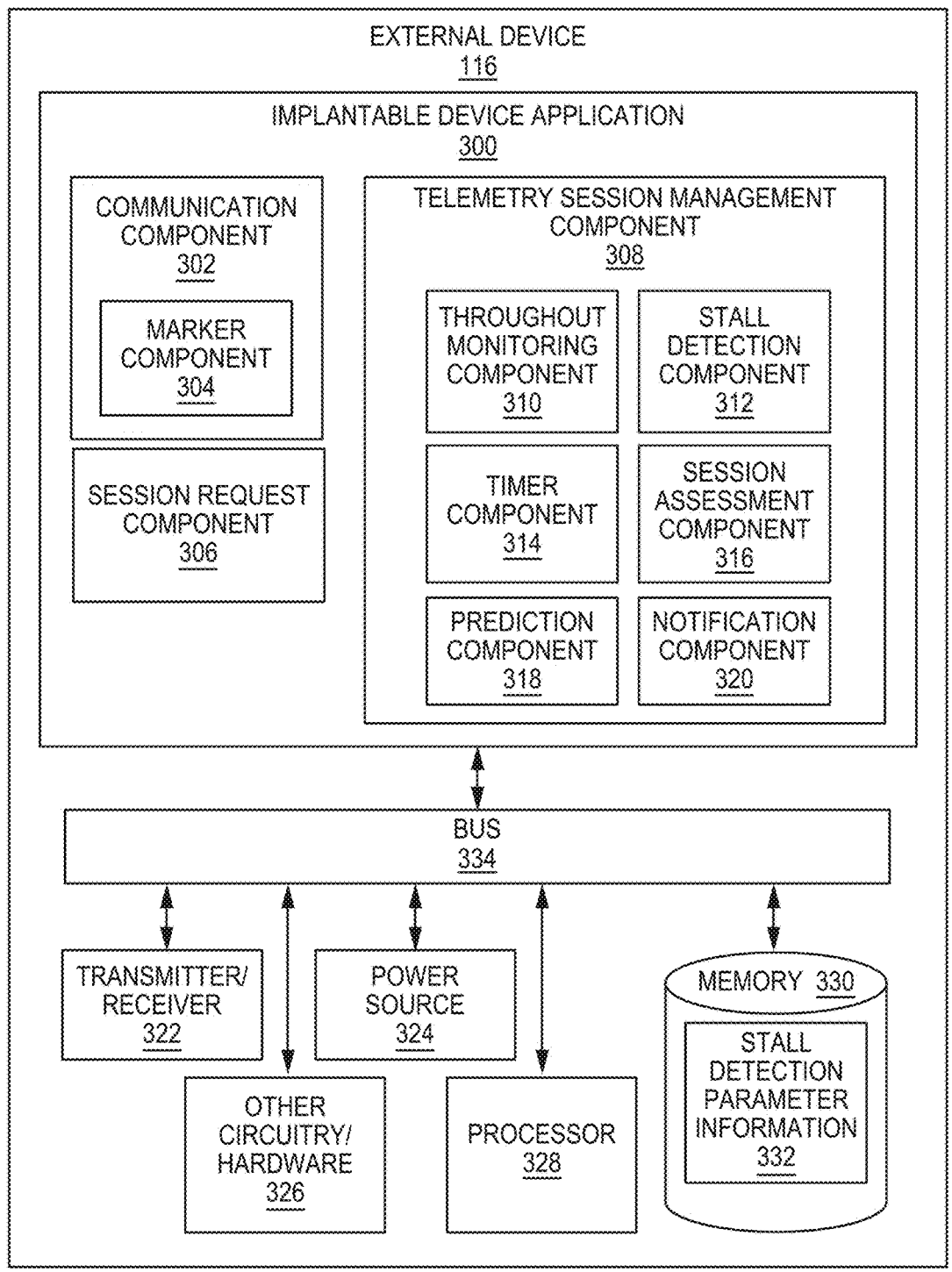
FIG. 3 illustrates a block diagram of an example, non-limiting external device in accordance with one or more embodiments described herein.

FIG. 3 illustrates a block diagram of an example, non-limiting external device (e.g., external device 116) in accordance with one or more embodiments described herein. The external device 116 can include an implantable device application 300 that is configured to provide various services associated with an implantable device (e.g., implantable device 104). In accordance with the subject disclosure, at least one of these services can include performing telemetry with an implantable device. In some embodiments, the implantable device application 300 can also facilitate receiving one or more services and/or access to information provided by a remote server device (e.g., not shown). According to these embodiments, the remote server device can provide one or more services and/or information related to an implantable device and/or a patient wearing an implantable device. For example, the remote server device can maintain information regarding patient identities, implantable device respectively worn by patients, and external devices and/or user accounts associated with the patients that are authorized to perform telemetry with the respective implantable devices. In another example, the remote server device can receive, collate and process information gathered by implantable devices (e.g., implantable device 104).

The external device 116 can also includes a transmitter/receiver 322 (or transceiver), a power source 324, and other device circuitry/hardware 326. The external device 116 can further include memory 330 configured to store computer executable components and instructions (e.g., the implantable device application 300) and a processor 328 to facilitate operation of the instructions (e.g., computer executable components and instructions) by the external device 116. The external device 116 can include a bus 334 that couples the various components of the implantable device 104, including, but not limited to, the implantable device application 300, the transmitter/receiver 322, the power source 324, the other device circuitry/hardware 326, the processor 328 and the memory 330. Repetitive description of like elements employed in other embodiments described herein is omitted for sake of brevity.

In the embodiment shown, the implantable device application 300 includes communication component 302, session request component 306 and telemetry session management component 308. Similar to the communication component 200 of the implantable device 104, communication component 302 can be configured to facilitate telemetry communication between the external device 116 and one or more implantable devices (e.g., implantable device 104). The communication component 302 can also facilitate wired and/or wireless communication between the external device and one or more other external devices (e.g., a remote server device and various other types of devices). For example, the communication component 302 can be configured to control operation of the transmitter/receiver 322 (or transceiver) to facilitate establishing a telemetry connection with the implantable device 104 and controlling transmission and reception of data packets by the external device 116. The type of the transmitter/receiver 322 can vary depending on the type of telemetry protocol the implantable external device is configured to employ. In some embodiments, the transmitter/receiver 322 can be configured to perform different types of telemetry protocols (e.g., proprietary, non-proprietary, BLUETOOTH®, BLE, Wi-Fi, cellular, etc.). In other embodiments, the external device 116 can include a plurality of different transmitters/receivers that are respectively configured to perform different types of telemetry communication protocols. In some embodiments, rather than including a transmitter and a receiver that do not share common circuitry, the external device 116 can include a transceiver.

The communication component 302 can be configured to facilitate telemetry communication between the external device 116 and an implantable device 104 using a variety of telemetry communication protocols including proprietary and non-proprietary telemetry protocols. For example, in one or more embodiments, communication component 302 can communicate with external device 116 using NFC, or another type of communication protocol over a PAN or a LAN (e.g., a Wi-Fi network) that can provide for communication over greater distances than NFC protocol or that can provide various advantages (such as increased security).

In some embodiments, the communication component 302 can control transmission and reception of data packets via a communication channel associated with a communication protocol utilizing lower energy consumption than a conventional communication protocol for wirelessly transmitting data. For example, in a non-limiting example, communication component 302 controls transmission and reception of data packets using BLE protocol. Other communication protocols that can be employed by communication component 302 to communicate with an implantable device or another device can include, but are not limited to, other BLUETOOTH® communication protocols, a Session Initiation Protocol (SIP) based protocol, a Zigbee® protocol, a RF4CE protocol, a WirelessHART protocol, a 6LoWPAN (IPv6 over Low power Wireless Personal Area Networks) protocol, a Z-Wave protocol, an ANT protocol, an ultra-wideband (UWB) standard protocol, a radio frequency (RF) communication protocol, and/or other proprietary and non-proprietary communication protocols.

The implantable device application 300 can include session request component 306 to facilitate sending connection requests to an implantable device. For example, in one or more embodiments, in order to connect to or otherwise initiate a telemetry session with an implantable device using a non-proprietary telemetry communication protocol (e.g., BLE), a user of the external device 116 can open the implantable device application 300 and select a "connection request" function of the application. In some implementation, in order to employ the implantable device application 300 to initiate a connection request, the user of the implantable device application 300 must have a registered user account and be logged in to his or her user account (e.g., based on entry of username/password information or the like). Based on selection of the connection request function, in some implementations, the session request component 306 can identify any implantable devices are within transmission range of the external device 116. The session request component 306 can further present information identifying the one or more nearby implantable devices. Using the implantable device application 300, the user can the select a particular identified implantable device to connect to and select a "request connection" soft button or otherwise provide some form or input that is interpreted by the session request component 306 as a request to establish a connection with the selected implantable device. In some implementations, the connection request can further identify or indicate a type of telemetry session being requested (e.g., a read only session, a read and program session, a monitoring session, clinician session, etc.). Based on the input, the session request component 306 can be configured to direct the communication component 302 to configure and send (e.g., using the transmitter/receiver 322) the connection request to the implantable device in accordance with the telemetry communication protocol employed by the external device 116 and the implantable device 104 (e.g., BLE).

In some embodiments, if the external device and/or the particular user account employed by the user was previously paired with the implantable device, the session request component 306 can direct the communication component 302 to establish a secure telemetry connection with the implantable device using previously determined encryption keys for the external device and/or user account and the implantable device 104. In implementations in which the external device 116 and/or the user account has not been paired with the implantable device, the session request component 306 can direct the communication component 302 to pair the external device 116 with the implantable device prior to performing a secure telemetry session with the implantable device.

The telemetry session management component 308 can be configured to facilitate managing one or more aspects of a telemetry session between the external device 116 and an implantable device (e.g., implantable device 104). The telemetry session management component 308 can include substantially same or similar components and perform substantially same or similar functions as the telemetry session management component 204. For example, in the embodiment shown, the telemetry session management component 308 can include throughput monitoring component 310, stall detection component 312, timer component 314, session assessment component 316, and prediction component 318. In one or more embodiments, the throughput monitoring component 310, the stall detection component 312, the timer component 314, the session assessment component 316, and the prediction component 318 can respectively provide same or similar features and functionalities of the throughput monitoring component 206, the stall detection component 208, the timer component 210, the session assessment component 212, and the prediction component 214.

For example, in one or more embodiments, the throughput monitoring component 310 can be configured to monitor uplink throughput associated with transmission (or lack thereof) of data by the external device 116 to the implantable device 104 during a telemetry session. In particular, after the external device 116 has established a telemetry connection or link (or in some embodiments, a secure telemetry connection or link), with an implantable device 104, the throughput monitoring component 310 can be configured to begin monitoring uplink throughput associated with data transmitted (or not transmitted) by the external device 116 to the implantable device 104 during the telemetry session. For example, the throughput monitoring component 310 can regularly or continuously determine the uplink throughput over the course of the telemetry session (e.g., every N milliseconds or seconds). As discussed above, various factors can affect the uplink throughput. In some embodiments, the throughput monitoring component 310 can be configured to determine the uplink throughput based on a number of application data packets successfully transmitted by the external device 116 (e.g., via communication component 302) to the implantable device 104 per connection interval. In another embodiment, the throughput monitoring component 310 can be configured to determine the uplink throughput based on a number of application data packets successfully transmitted by the external device 116 (e.g., via communication component 302) to the implantable device 104 device every M seconds (e.g., 5 seconds, 10 seconds, etc.). The throughput monitoring component 310 can also determine the uplink throughput based on an amount of data per packet. In some implementations, the implantable device 104 can be configured to send the external device an acknowledgement message each time it receives a data transmission from the external device 116. With these implementations, data transmission by the external device 116 to the implantable device 104 can be considered successful based on reception of an acknowledgment message for that data transmission. Thus in some embodiments, the throughput monitoring component 310 can be configured to determine the uplink throughput based on reception of acknowledgment messages acknowledging successful transmission of data packets by the external device 116. The throughput monitoring component 310 can also be configured to determine the uplink throughput based on timing of reception of the acknowledgment messages.

In other embodiments, the throughput monitoring component 310 can be configured to determine the uplink throughput based on time delays between successful transmissions of data packets by the external device 116 to the implantable device 104. For example, the throughput monitoring component 310 can determine the uplink throughput as a function of average duration of time between successful transmissions of data packets.

The telemetry session management component 308 can include timer component 314 to track the progression of time during a telemetry session. For example, the timer component 314 can track the duration of the telemetry session beginning at the point of establishment of the telemetry connection. The timer component 314 can also track occurrence of communication events and duration of time between communication events. For example, the timer component 314 can track timing of unsuccessful data transmissions (wherein an acknowledgment message was expected but not received), timing of successful data transmissions (wherein an acknowledgment message was expected and received), timing between transmission successful data transmissions, timing of reception of acknowledgment messages, timing of reception of other downlinks, and the like.

Like the stall detection component 208, the stall detection component 312 can regularly or continuously evaluate the session uplink throughput as determined by the throughput monitoring component 310. The stall detection component 312 can further determine if a telemetry session has stalled based on the monitored uplink throughput. In this sense, the stall detection component 312 can detect a lack of progress in a telemetry session based on no or low uplink data transmissions successfully performed by the external device 116. In one implementation, the stall detection component 312 can be configured to detect or determine that a telemetry session has stalled if the uplink throughput falls below a defined threshold amount or level. For example, if the throughput monitoring component 310 determines that the telemetry session throughput is X bps and X is less than or equal to the threshold value of Y bps, then stall detection component 312 can determine that the telemetry session has stalled. In another implementation, the stall detection component 312 can be configured to detect or determine that a telemetry session has stalled if the uplink throughput falls below a defined threshold amount or level for a predefined duration, referred to herein as the "stall period." For example, if the throughput monitoring component 310 determines that the telemetry session throughput is X bps or less for more than the stall period of Z seconds or minutes and X is less than or equal to the threshold value of Y, then stall detection component 312 can determine that the telemetry session has stalled. The threshold values or levels for the minimum uplink throughput (e.g., Y) and the stall period duration (Z), can be predefined and stored in memory 330 of the external device 116. For example, in the embodiment shown, the memory 330 can include a data structure or cell that includes stall detection parameter information 332. The stall detection parameter information 332 can include information or rules that define how the throughput monitoring component 310 should measure uplink throughput (e.g., number data of successful data packets per millisecond or second, timing or reception of acknowledgment messages, timing between successful transmission of data packets, etc.), and how the stall detection component 312 should determine whether a telemetry stall has occurred (e.g., the threshold amount for minimal uplink throughput and/or duration or time for which the uplink throughput can be less than the threshold amount).

In another implementation, in which the throughput monitoring component 310 is configured to monitor average duration of time between successful transmissions of data packets, the stall detection component 312 can be configured to determine that a telemetry session has stalled based on the average duration of time being below a threshold level. In yet another implementation, in which the throughput monitoring component 310 is configured to monitor duration of time between successful transmissions of data packets, the stall detection component 312 can determine the telemetry session has stalled based on a pattern in the duration of time between successful transmissions of data packets that indicates a session stall. For example, the stall detection component 312 can be configured to detect a stalled telemetry session based on a significant drop (e.g., with respect to a threshold degree of deviation) in successful data transmissions by the external device 116.

Based on detection of a stall event, the stall detection component 312 can be configured to direct the communication component 302 to disable or terminate the telemetry connection. For example, in response to detection of the uplink throughput being below a defined threshold amount or being below a defined threshold amount for a maximum stall period, the stall detection component 312 can direct the communication component 302 to terminate the telemetry connection between the implantable device 104 and the external device 116. The communication component 302 can be configured to respond accordingly by terminating or otherwise disabling the telemetry connection between the implantable device 104 and the external device 116. For example, in one implementation, the communication component 302 can disable the telemetry connection by temporarily turning off the transmitter/receiver 322.

In some embodiments, like the telemetry session management component 204, the telemetry session management component 308 can employ different criteria for detecting stalled telemetry sessions based on the type of telemetry session being performed between the implantable device 104 and the external device 116. For example, in one or more implementation, the external device 116 can be configured to perform different types of telemetry sessions with the implantable device 104, such as read-only sessions, read and program sessions, read and control sessions, program only sessions, monitoring session, clinician session, and the like. According to these embodiments, the session assessment component 316 can be configured to evaluate a connection request and/or other data associated with the telemetry session to determine a "type" of the telemetry session. The type of the telemetry session can further control the specific stall detection criteria (e.g., uplink throughput minimum thresholds, stall periods, thresholds/requirements for time delays between transmissions, etc.) employed by the stall detection component 312 to determine if and when the telemetry session has stalled. Information associating different defined types of telemetry sessions and the specific stall detection criteria can further be stored in memory 330 (e.g., as stall detection parameter information 332). The stall detection component 312 can further select the appropriate stall detection parameter information (e.g., uplink throughput minimum threshold and stall period, minimum average duration between successful transmission of data packets, etc.) to apply for evaluating the uplink throughput based on the type of the telemetry session, as determined by the session assessment component 316.

In addition, the criteria employed by the external device 116 and the implantable device 104 to detect telemetry session stall for can vary between the respective devices. For example, depending on the type of the telemetry session, the implantable device 104 can be prompted to provide the external device 116 uplink transmissions at a much higher rate than the external device 116 is prompted to provide the implantable device uplink transmissions. According to this example, both the external device 116 (e.g., via throughput monitoring component 310) and the implantable device (e.g., via throughput monitoring component 206), can be configured to monitor uplink throughput over the course of a telemetry session conducted between them. However, the minimum uplink throughput threshold applied by the external device (e.g., via the stall detection component 312) to detect a stall in the telemetry session can be lower than the minimum uplink throughput threshold applied by the implantable device (e.g., via the stall detection component 208) to detect a stall in the telemetry session.

The prediction component 318 can further provide for predicting stall events based on the monitored uplink throughput information in a same or similar manner as prediction component 214. For example, the prediction component 318 can be configured to identify characteristics of the monitored uplink throughput information that indicate the onset of a possible stall event. The prediction component 318 can further facilitate initiating remedial action by the communication component 302 to prevent the possible stall event or minimize harm associated with occurrence of the stall event. For instance, in one implementation, based on detection of one or more defined characteristic that indicate a possible stall event may occur, the prediction component 318 can notify the communication component 302 that a possible stall event has been predicted. Based on the notification, the communication component 302 can be configured to prioritize the transmission of data to the implantable device 104 such that data considered more critical than other data is communicated first. According to this implementation, the communication component 302 can access information stored in memory 330 that identifies a priority classification associated with different types of data and transmit data having a higher priority classification before transmission of data having a lower priority classification.

In another implementation, the telemetry session management component 308 can include notification component 320 to facilitate generating and rendering, at the external device 116, notifications regarding predicted telemetry session stalls. According to these implementations, based on detection of an onset of a stall event, the notification component 320 can be configured to generate a warning message that informs a user of the external device 116 regarding the degradation of uplink throughput. For example, the warning message can inform the user of the external device 116 that uplink throughput is low. The notification component 320 can further be configured to generate a prompt that can be presented to a user of the external device 116 (e.g., via a display of the external device, via an audible signal, or another suitable output mechanism) based on reception of the warning message. For example, the prompt can inform the user of the external device 116 that uplink throughput is low. Based on reception of the prompt, the user of the external device can take action to facilitate improving the uplink throughput, such as moving the external device 116 closer to the implantable device 104, or moving the external device 116 and the implantable device 104 (e.g., by moving the patient in which the implantable device 104 is implanted) to an area that is associated with less interference.

In another implementation, based on detection of a possible stall event by the prediction component 318, the communication component 302 can be configured to backup critical information associated with the telemetry session. For example, the communication component 302 can make copies of critical data that is queued for transmission to the implantable device 104. In some embodiments, the communication component 302 can also include marker component 304 to place markers where data transmission was terminated in response to a determination that a stall event has occurred (e.g., by the stall detection component 312). For example, the marker component 304 can be configured to generate information that identifies data that was attempting to be transmitted to the implantable device 104 and/or was queued for transmission to the implantable device 104 at the point when the telemetry session stalled. This maker information can further be stored in memory 330. Accordingly, if the telemetry session is reinitiated, the communication component 302 can access the marker information and begin transmitting data to the implantable device 104 at the point where the telemetry session was terminated.

The external device 116 can further include a suitable power source 324 to drive the functionality of the external device 116 and to provide power to the various electrical components of the external device 116. In one or more embodiments, the power source 324 includes but is not limited to, a battery, a capacitor, a charge pump, a mechanically derived power source (e.g., microelectromechanical systems (MEMs) device), or an induction component. The external device 116 can also include various other device circuitry/hardware 326 to facilitate operation of the various components of the external device 116. For example, the other device circuitry/hardware 326 can include one or more suitable input devices (e.g., touchscreen, hard buttons, soft buttons, voice input), a display, an RFID reader, a biometric reader, a camera, and various other types of hardware elements found in conventional smart phones, tablets, laptop PCs, VR devices, wearable physiological monitoring devices, and the like, examples of which can be found with reference to FIG. 10.

Figure 4:
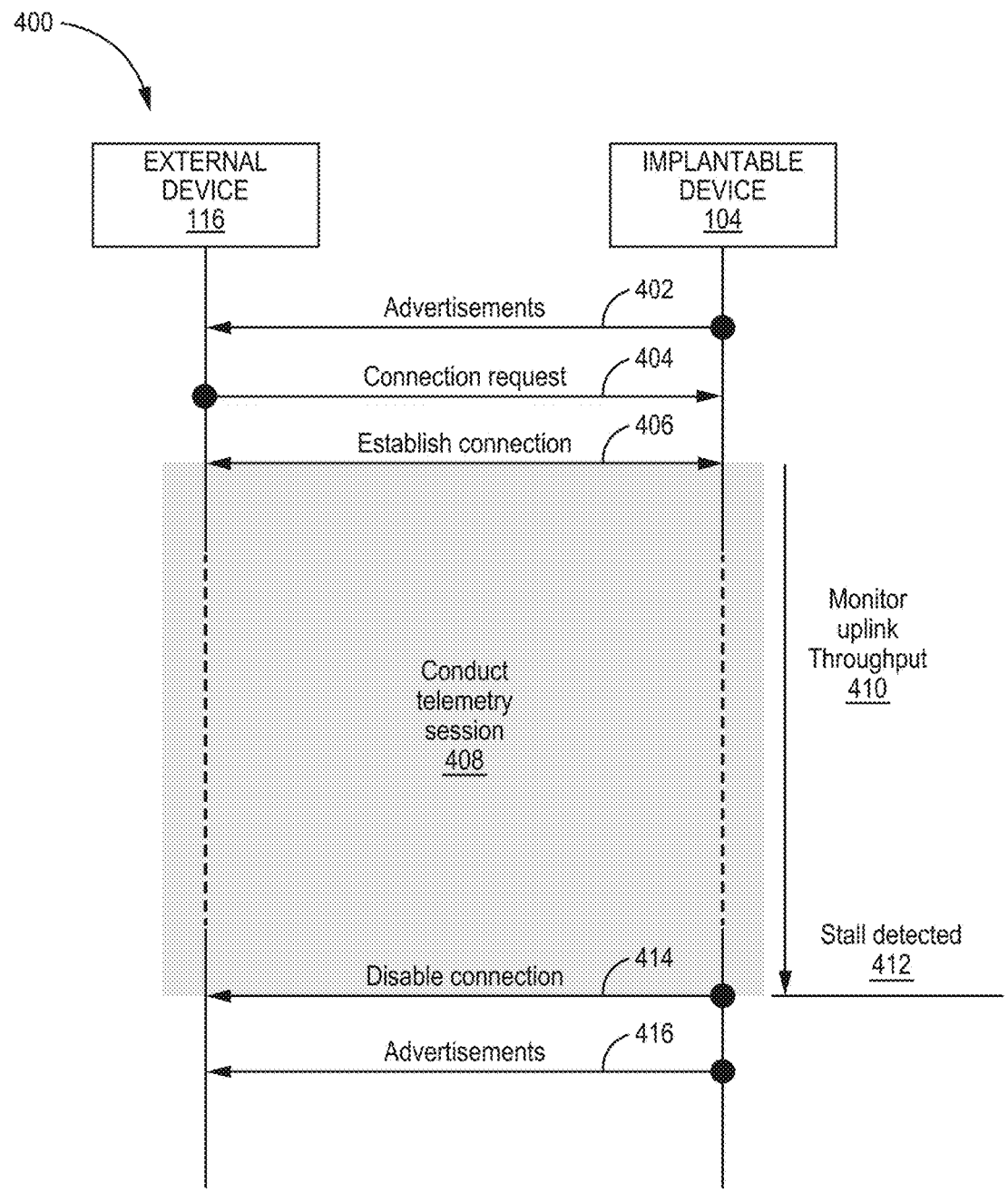
FIG. 4 illustrates a signaling diagram of an example, non-limiting process for establishing and disabling a telemetry connection between an implantable device and an external device in accordance with one or more embodiments described herein.

FIG. 4 illustrates a signaling diagram 400 of an example, non-limiting process for establishing and disabling a telemetry connection between an implantable device (e.g., implantable device 104) and an external device (e.g., external device 116) in accordance with one or more embodiments described herein. Signaling diagram 400 is particularly directed to a perspective wherein an implantable device 104 monitors uplink throughput associated with performance of a telemetry session with an external device 116 and disables the connection based on detection of a stall in the telemetry session.

With reference to FIG. 4, at 402, the implantable device 104 can send advertisements to the external device in accordance with an advertisement mode associated with the telemetry protocol employed by the implantable device and the external device to communicate. For example, in embodiments in which the implantable device 104 and the external device 116 are configured to employ BLE, the implantable device 104 can be configured to operate in an advertisement mode wherein the implantable device 104 regularly transmits advertisement signals or beacons that indicate the implantable device 104 is ready and available to perform telemetry. Based on detection of an advertisement signal by the external device 116, at 404, the external device 116 can send a connection request to the implantable device 104. Based on reception of the connection request, at 406 the implantable device 104 can establish a connection with the external device 116. The procedure for establishing the connection at 506 can vary. In one or more embodiments, the implantable device 104 is configured to establish a secure, trusted telemetry connection with the external device (e.g., external device 116) prior to facilitating the exchange of sensitive data between the implantable device 104 and the external device using a non-proprietary telemetry communication protocol (e.g., BLUETOOTH®, BLE, and the like). Thus in some embodiments, at 404, in order to establish such a secure, trusted connection, the implantable device 104 must first be paired with the external device (or otherwise have established a trusted relationship with the external device performing an authorization and authentication procedure).

After the implantable device 104 and the external device 116 have established a telemetry connection at 406 (or in some embodiments, a secure telemetry connection), the respective devices can conduct the telemetry session at 408. The flow of communications between the respective devices in association with conducting the telemetry session at 408 can vary depending on the type of the telemetry session and in some implementations, the activity of the user of the external device 116. For example, in one or more implementations in which the telemetry session is a monitoring session, after the respective devices establish the telemetry connection at 406, the external device 116 can be configured to send the implantable device 104 an interrogation request that is a request for data from the implantable device. If the interrogation request is received by the implantable device 104, the implantable device 104 is configured to respond by transmitting the external device 116 the requested data. In some implementations, based on reception of the data from the implantable device 104, the external device 116 can be configured to transmit an acknowledgment message. This process can repeat one or more times over the one or more connection intervals until the external device 116 has completed requesting and receiving all desired data from the implantable device 104 or until the connection is terminated based on detection of a stall event (e.g., as exemplified at 412).

In another example implementation, the telemetry session can be a clinician session performed by a clinician in association with an in-office visit by a patient wearing the implantable device 104. According to this example implementation, after the respective devices establish the telemetry connection at 406, the external device 116 may send the implantable device 104 an interrogation request that is a request for waveform data from the implantable device 104. If the waveform data request is received by the implantable device 104, the implantable device 104 will begin sending the external device 116 the waveform data as requested. The implantable device 104 can be configured to transmit the waveform data to the external device 116 until the session is ended or the external device instructs the implantable device to stop sending the waveform data. Over the course of the patient visit, the clinician may review the waveform data and examine the patient. At some point the during the patient visit, using the external device 116, the clinician may also send one or more additional interrogation requests to the external device 116 for other data stored in memory of the implantable device. Based on reception of the interrogation requests, the implantable device can respond accordingly by providing the requested data. In another implementation, using the external device 116, the clinician may also send one or more programming or control commands to the implantable device 104. Based on reception of the control or programming commands, the implantable device 104 can respond accordingly by applying the control or programming commands and sending the external device confirmation of the completed programming.

Regardless of the type of the telemetry session, after the connection is established at 406, at 410 the implantable device 104 can be begin monitoring uplink throughput associated with data successfully transmitted (or not successfully transmitted) by the implantable device 104 to the external device 116 over the course of the telemetry session. The implantable device 104 can continue to monitor the uplink throughput over the course of the telemetry session. For example, the implantable device 104 can regularly or continuously determine the uplink throughput over the course of the telemetry session.

At 412, the implantable device detects a stall in the telemetry session based on the monitored uplink throughput and predefined stall detection parameter information. The stall detection parameter information (e.g., the minimum uplink threshold amounts, the stall period, the maximum average time between data transmissions, etc.) can vary based on the type of the telemetry session. For example, in one example embodiment, at 412 the implantable device 104 can determine (e.g., via stall detection component 208) that the telemetry session has stalled based on a determination that the average duration of time between successful data transmissions has fallen below a threshold duration or based on a determination of a significant (relative to threshold degree of deviation) drop in frequency of successful data transmissions.

In another example embodiment, at 412, the implantable device 104 can determine (e.g., via stall detection component 208) that the telemetry session has stalled based on a determination that the implantable device uplink throughput is below a defined threshold level for a defined stall period. For example, in an implementation in which the telemetry session is a monitoring session, the defined threshold level may be N bps and the stall period may be M seconds. According to this example, a variety conditions could cause the uplink throughput to fall below N bps for M second during a telemetry session. For example, the respective devices may move out of transmission range, the connection may be disturbed by interference, or the external device could stop providing the implantable device with downlinks (e.g., interrogation requests) that prompt the implantable device to send uplink transmissions. In another example, in another implementation in which the telemetry session is a clinician session, the defined threshold level may be X bps and the stall period may be Y minutes. According to this example, a variety conditions could cause the uplink throughput to fall below X bps for Y minutes during a telemetry session. For example, the respective devices may move out of transmission range. For instance, in furtherance to the clinician session example above, the clinician may walk out of the patient's room to attend to another patient without closing the telemetry session. However, based on the nature of the clinician session, the implantable device 104 may assume the clinician is still interacting with the patient and keeping the session active to receive and review waveform data. Thus the implantable device 104 can be configured to keep the telemetry connection active until the stall period runs out (which could be on the order of several minutes as opposed to about a 10 second timer associated with a monitoring session). In another example, the connection may be disturbed by interference, or the external device 116 could stop providing the implantable device with downlinks (e.g., interrogation requests) that prompt the implantable device to send uplink transmissions.

Regardless of the reason for the drop in uplink throughput and the type of the telemetry session, at 412 based on detection of the stall in the telemetry session, at 414 the implantable device 104 can automatically disable the telemetry connection. In the embodiment shown, the implantable device 104 can then return to the advertisement mode and begin sending advertisements again at 416 to facilitate establishing a new telemetry connection with the implantable device.

Figure 5:
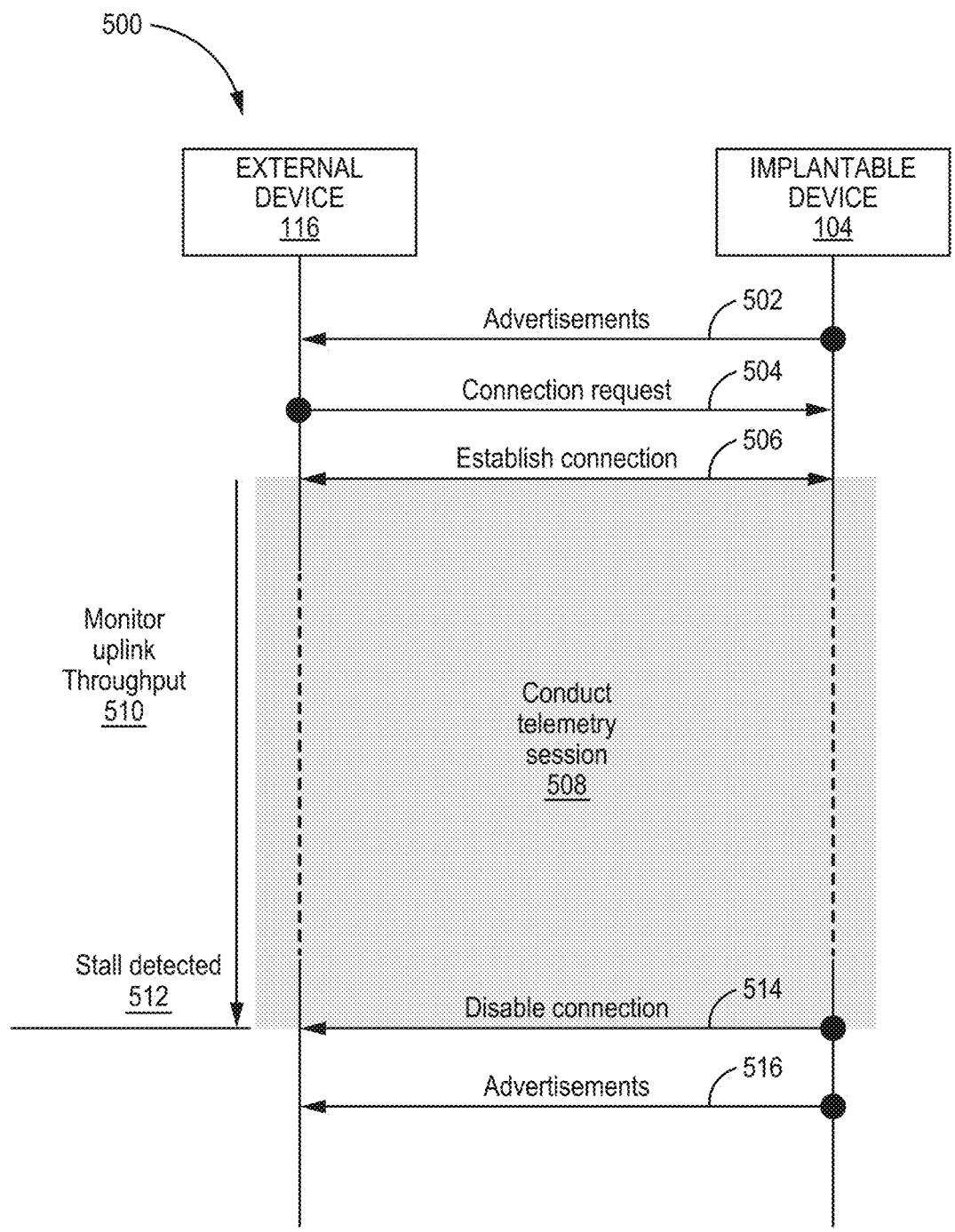
FIG. 5 illustrates a signaling diagram of an example, non-limiting process for establishing and disabling a telemetry connection between an implantable device and an external device in accordance with one or more embodiments described herein.

FIG. 5 illustrates a signaling diagram 500 of an example, non-limiting process for establishing and disabling a telemetry connection between an implantable device (e.g., implantable device 104) and an external device (e.g., external device 116) in accordance with one or more embodiments described herein. Signaling diagram 500 is particularly directed to a perspective wherein an external device 116 monitors uplink throughput associated with performance of a telemetry session with an implantable device 104 and disables the connection based on detection of a stall in the telemetry session. For example, as described with reference to FIG. 4 and signaling diagram 400, in one embodiment, the implantable device 104 can determine that the telemetry session has stalled based on a determination that the implantable device uplink throughput is below a first defined threshold level for a first defined stall period. However, as exemplified in FIG. 5 and signaling diagram 500, in other embodiments the external device 116 can also be configured to monitor uplink throughput associated with performance of the telemetry session with the implantable device 104 and disable the connection based on detection of a stall in the telemetry session. For example, in one embodiment, the external device 116 can determine that the telemetry session has stalled based on a determination that the external device uplink throughput is below a second threshold level for a second stall period. In some implementations the first and second uplink throughput threshold and the first and second stall periods can be the same. In other implementations, the first and second uplink throughput threshold and the first and second stall periods can be the different. Repetitive description of like elements employed in respective embodiments is omitted for sake of brevity.

With reference to FIG. 5 at 502, the implantable device 104 can send advertisements to the external device in accordance with an advertisement mode associated with the telemetry protocol employed by the implantable device and the external device to communicate. Based on detection of an advertisement signal by the external device 116, at 504, the external device 116 can send a connection request to the implantable device 104. Based on reception of the connection request, at 506 the implantable device 104 can establish a connection with the external device 116. The procedure for establishing the connection at 506 can vary. In one or more embodiments, the implantable device 104 is configured to establish a secure, trusted telemetry connection with the external device (e.g., external device 116) prior to facilitating the exchange of sensitive data between the implantable device 104 and the external device using a non-proprietary telemetry communication protocol (e.g., BLUETOOTH®, BLE, and the like). Thus in some embodiments, at 506, in order to establish such a secure, trusted connection, the external device 116 must first be paired with the implantable device. After the implantable device 104 and the external device 116 have established a telemetry connection at 506 (or in some embodiments, a secure telemetry connection), the respective devices can conduct the telemetry session at 508. The flow of communications between the respective devices in association with conducting the telemetry session at 508 can vary depending on the type of the telemetry session.

Regardless of the type of the telemetry session, after the connection is established at 506, at 510 the external device 116 can be begin monitoring uplink throughput associated with data transmitted by the external device 116 to the implantable device 104 over the course of the telemetry session. The external device 116 can continue to monitor the uplink throughput over the course of the telemetry session. For example, the external device 116 can regularly or continuously determine the uplink throughput over the course of the telemetry session. At 512, the external device 116 detects a stall in the telemetry session based on the uplink throughput. For example, in one embodiment, the external device 116 can determine that the telemetry session has stalled based on a determination that the implantable device uplink throughput is below a second threshold level for a second stall period (e.g., as defined based on a second stall period). The second threshold level and the second stall period can vary based on the type of the telemetry session. At 514, based on a determination that the telemetry session has stalled, the external device 116 can automatically disable the telemetry connection. In the embodiment shown, the implantable device 104 can then return to the advertisement mode and begin sending advertisements again at 516 to facilitate establishing a new telemetry connection with the implantable device 104.

FIGS. 6-9 illustrate additional flow diagrams of example, non-limiting methods that facilitate mitigating implantable device power drain associated with stalled telemetry sessions in accordance with one or more embodiments described herein. While, for purposes of simplicity of explanation, the methodologies are shown and described as a series of acts, the disclosed subject matter is not limited by the order of acts, as some acts can occur in different orders and/or concurrently with other acts from that shown and described herein. For example, those skilled in the art will understand and appreciate that a methodology can alternatively be represented as a series of interrelated statuses or events, such as in a state diagram. Moreover, not all illustrated acts may be required to implement a methodology in accordance with the disclosed subject matter. Additionally, it is to be appreciated that the methodologies disclosed in this disclosure are capable of being stored on an article of manufacture to facilitate transporting and transferring such methodologies to computers or other computing devices.

Figure 6:
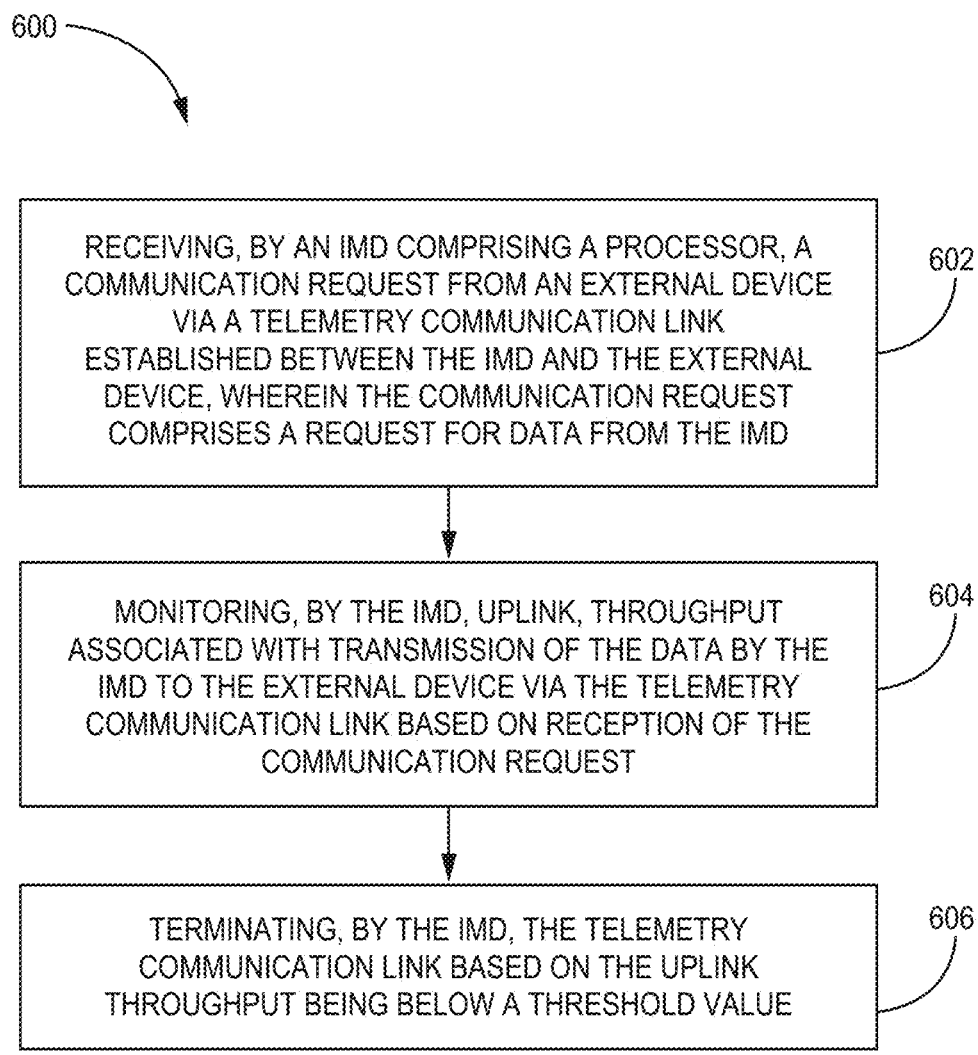
FIGS. 6-9 illustrate additional flow diagrams of example, non-limiting methods that facilitate mitigating implantable device power drain associated with stalled telemetry sessions in accordance with one or more embodiments described herein.

Referring now to FIG. 6, shown is a flow diagram of an example method 600 configured to facilitate mitigating implantable device power drain associated with stalled telemetry sessions in accordance with one embodiment. In some embodiments of method 600, an implantable device (e.g., implantable device 104) employs a communication component (e.g., communication component 200), and a telemetry session management component (e.g., telemetry session management component 204) to facilitate detecting and disabling a stalled telemetry session between the implantable device (e.g., implantable device 104) and an external device (e.g., external device 116). Repetitive description of like elements employed in other embodiments described herein is omitted for sake of brevity.

At 602, an IMD comprising a processor, receives a communication request from an external device via a telemetry communication link established between the IMD and the external device, wherein the communication request comprises a request for data from the implantable medical device. For example, the communication request can comprises a request for physiological data monitored by the implantable device or information regarding performance statistics monitored by the implantable device. At 604, the IMD monitors uplink throughput associated with transmission of the data by the implantable medical device to the external device via the telemetry communication link based on reception of the communication request. For example, the IMD can determine an amount of the data that is successfully transmitted to the external device every X seconds, durations between successful transmissions of data packets comprising the data, an amount of successful data transmitted per connection interval, or the like. At 606, the IMD can terminate the telemetry communication link based on the uplink throughput being below a threshold value. In some implementations, the IMD can be configured to terminate the communication link based on the uplink throughput being below the threshold value for a defined stall period.

Figure 7:
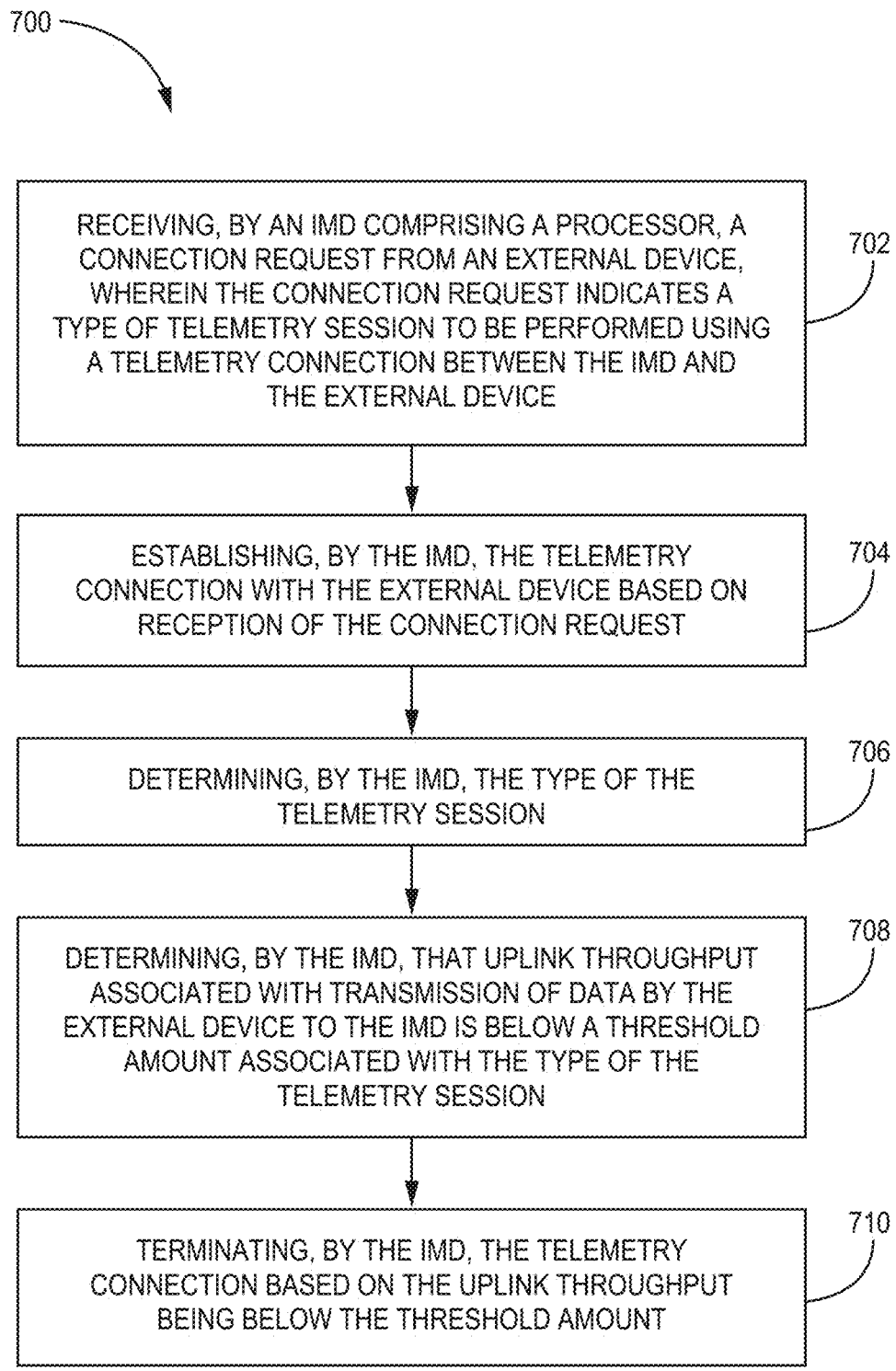

Turning now to FIG. 7, shown is a flow diagram of another example method 700 configured to facilitate mitigating implantable device power drain associated with stalled telemetry sessions in accordance with one embodiment. In some embodiments of method 700, an implantable device (e.g., implantable device 104) employs a communication component (e.g., communication component 200), and a telemetry session management component (e.g., telemetry session management component 204) to facilitate detecting and disabling a stalled telemetry session between the implantable device (e.g., implantable device 104) and an external device (e.g., external device 116). Repetitive description of like elements employed in other embodiments described herein is omitted for sake of brevity.

At 702, an IMD comprising a processor (e.g., implantable device 104), receives a connection request from an external device (e.g., external device 116), wherein the connection request indicates a type of telemetry session to be performed using the telemetry connection between the IMD and the external device. At 704, the IMD establishes the telemetry connection with the external device based on reception of the connection request. At 706, the IMD determines the type of the telemetry session. For example, the IMD can determine if the telemetry session is a monitoring session or a clinician session. At 708, the IMD determines that the uplink throughput associated with transmission of data by the external device to the IMD is below a threshold amount associated with the type of the telemetry session. At 710, the IMD terminates the telemetry connection based on the uplink throughput being below the threshold amount.

Figure 8:
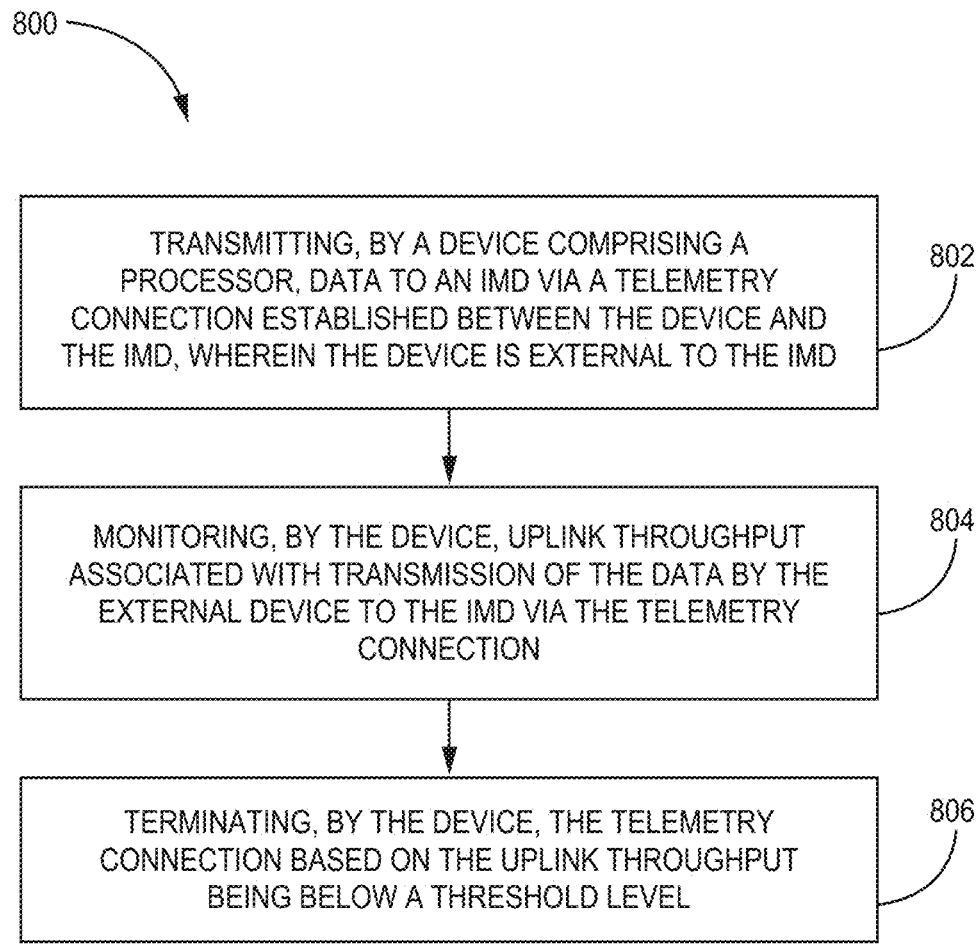

FIG. 8 shows a flow diagram of another example method 800 configured to facilitate mitigating implantable device power drain associated with stalled telemetry sessions in accordance with one embodiment. In some embodiments of method 800, an external device (e.g., external device 116) employs an implantable device application (e.g., implantable device application 300) to facilitate detecting and disabling a stalled telemetry session between the external device (e.g., external device 116) and the implantable device (e.g., implantable device 104). Repetitive description of like elements employed in other embodiments described herein is omitted for sake of brevity.

At 802, an device comprising a processor (e.g., external device 116), transmits data to an IMD via a telemetry connection established between the device and the IMD, wherein the device is external to the IMD. At 804, the device monitors uplink throughput associated with transmission of data by the external device to the IMD via the telemetry connection. At 806, the device terminates the telemetry connection based on the uplink throughput being below a threshold level.

Figure 9:
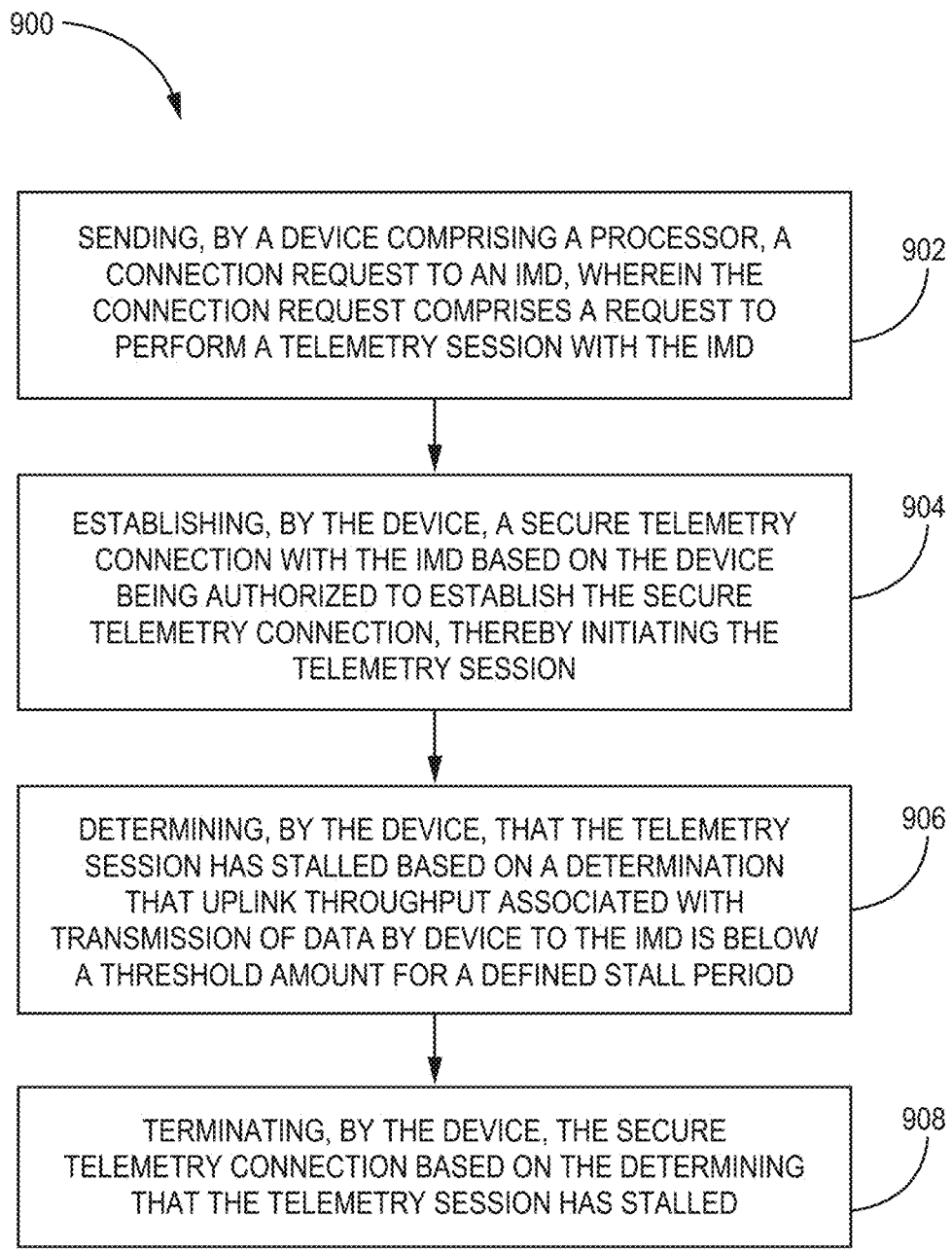

FIG. 9 shows a flow diagram of another example method 900 configured to facilitate mitigating implantable device power drain associated with stalled telemetry sessions in accordance with one embodiment. In some embodiments of method 900, an external device (e.g., external device 116) employs an implantable device application (e.g., implantable device application 300) to facilitate detecting and disabling a stalled telemetry session between the external device (e.g., external device 116) and the implantable device (e.g., implantable device 104). Repetitive description of like elements employed in other embodiments described herein is omitted for sake of brevity.

At 902, a device comprising a processor (e.g., external device 116), sends a connection request to an IMD, wherein the connection request comprises a request to perform a telemetry session with the IMD. At 904, the device establishes a secure connection with the IMD based on the device being authorized to establish the secure telemetry connection, thereby initiating the telemetry session. For example, in some implementations, the implantable device will only authorize establishment of the secure telemetry connection if the implantable device is paired with the external device or has otherwise performed an authorization/authentication procedure against the external device. At 908, the device determines that the telemetry session has stalled based on a determination that uplink throughput associated with transmission of data by the device to the IMD is below a threshold amount for a defined stall period. For example, in implementations, in which the telemetry session is a monitoring session, the stall period can be about 10 seconds and implementations in which the telemetry session is a clinician session, the stall period can be about 30 minutes. At 910, the device terminates the secure telemetry connection based on the determining that the telemetry session has stalled.

Figure 10:
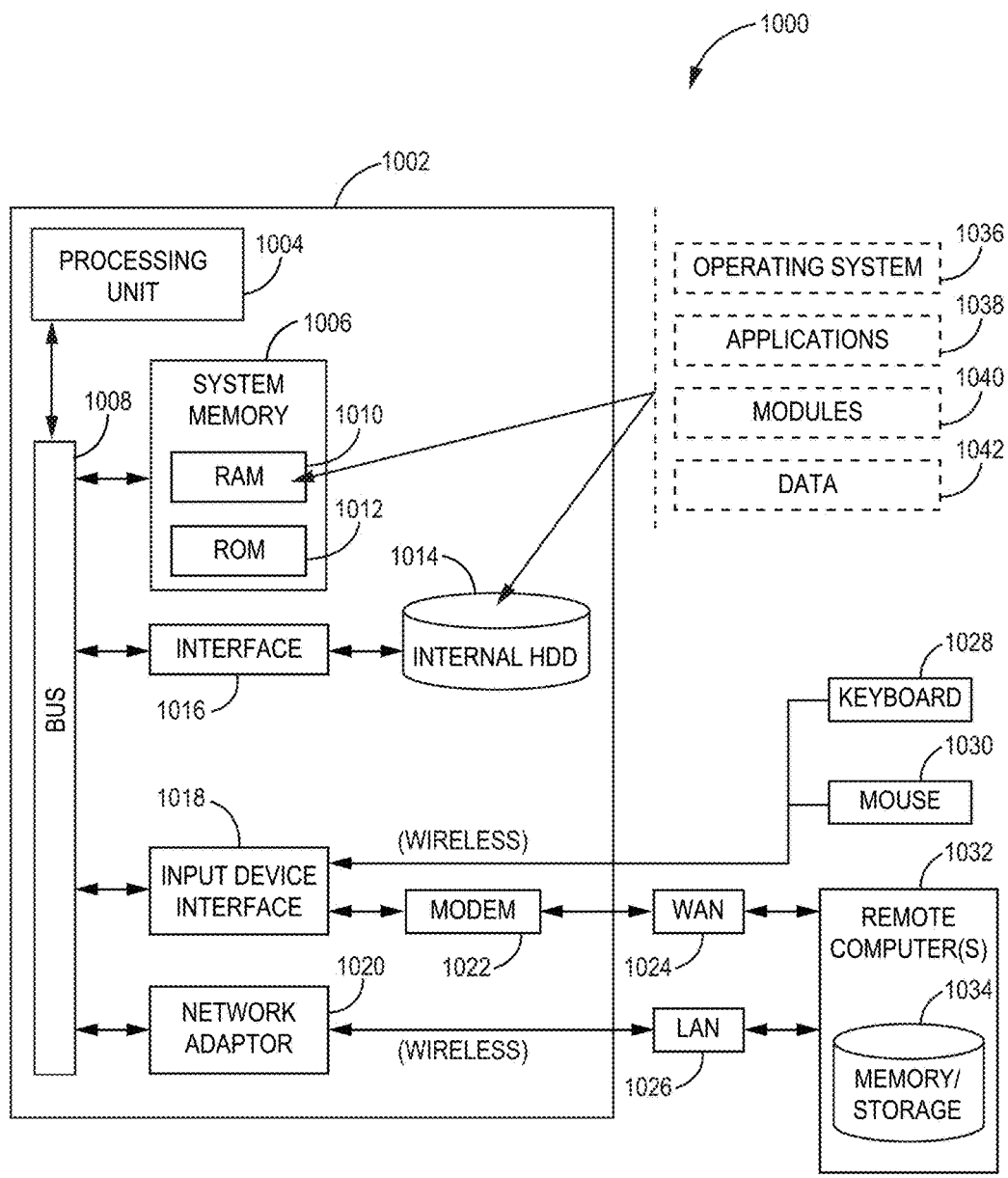
FIG. 10 illustrates a block diagram of an example, non-limiting computer operable to facilitate mitigating implantable device power drain associated with stalled telemetry sessions in accordance with one or more embodiments described herein.

FIG. 10 illustrates a block diagram of an example, non-limiting computer operable to facilitate telemetry overuse reduction in an implantable device in accordance with one or more embodiments described herein. For example, in some embodiments, the computer can be or be included within implantable device 104 and/or external device 116. Repetitive description of like elements employed in other embodiments described herein is omitted for sake of brevity.

In order to provide additional context for one or more embodiments described herein, FIG. 10 and the following discussion are intended to provide a brief, general description of a suitable computing environment 1000 in which the one or more embodiments described herein can be implemented.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

Computing devices typically include a variety of media, which can include computer-readable storage media and/or communications media, which two terms are used herein differently from one another as follows. Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data or unstructured data. Tangible and/or non-transitory computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD) or other optical disk storage, magnetic cassettes, magnetic tape, magnetic disk storage, other magnetic storage devices and/or other media that can be used to store desired information. Computer-readable storage media can be accessed by one or more local or remote computing devices, e.g., via access requests, queries or other data retrieval protocols, for a variety of operations with respect to the information stored by the medium.

In this regard, the term "tangible" herein as applied to storage, memory, computer-readable media or computer-readable storage media, is to be understood to exclude only propagating intangible signals per se as a modifier and does not relinquish coverage of all standard storage, memory, computer-readable media or computer-readable storage media that are not only propagating intangible signals per se.

In this regard, the term "non-transitory" herein as applied to storage, memory, computer-readable media or computer-readable storage media, is to be understood to exclude only propagating transitory signals per se as a modifier and does not relinquish coverage of all standard storage, memory, computer-readable media or computer-readable storage media that are not only propagating transitory signals per se.

Communications media typically embody computer-readable instructions, data structures, program modules or other structured or unstructured data in a data signal such as a modulated data signal, e.g., a channel wave or other transport mechanism, and includes any information delivery or transport media. The term "modulated data signal" or signals refers to a signal that has one or more of the data signal's characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 10, example environment 1000 that can be employed to implement one or more embodiments of the embodiments described herein includes computer 1002. Computer 1002 includes processing unit 1004, system memory 1006 and system bus 1008. System bus 1008 couples system components including, but not limited to, system memory 1006 to processing unit 1004. Processing unit 1004 can be any of various commercially available processors. Dual microprocessors and other multiprocessor architectures can also be employed as processing unit 1004.

System bus 1008 can be any of several types of bus structure that can further interconnect to a memory bus (with or without a memory controller), a peripheral bus, and a local bus using any of a variety of commercially available bus architectures. System memory 1006 includes RAM 1010 and ROM 1012. A basic input/output system (BIOS) can be stored in a non-volatile memory such as ROM, erasable programmable read only memory (EPROM), EEPROM, which BIOS contains the basic routines that help to transfer information between elements within computer 1002, such as during startup. RAM 1010 can also include a high-speed RAM such as static RAM for caching data.

Computer 1002 further includes internal hard disk drive (HDD) 1014 (e.g., Enhanced Integrated Drive Electronics (EIDE), Serial Advanced Technology Attachment (SATA)). HDD 1014 can be connected to system bus 1008 by hard disk drive interface 1016. The drives and their associated computer-readable storage media provide nonvolatile storage of data, data structures, computer-executable instructions, and so forth. For computer 1002, the drives and storage media accommodate the storage of any data in a suitable digital format.

A number of program modules can be stored in the drives and RAM 1010, including operating system 1036, one or more application programs 1038, other program modules 1040 and program data 1042. All or portions of the operating system, applications, modules, and/or data can also be cached in RAM 1010. The systems and methods described herein can be implemented utilizing various commercially available operating systems or combinations of operating systems.

A mobile device can enter commands and information into computer 1002 through one or more wireless input devices, e.g., wireless keyboard 1028 and a pointing device, such as wireless mouse 1030. Other input devices (not shown) can include a smart phone, tablet, laptop, wand, wearable device or the like. These and other input devices are often connected to the processing unit 1004 through input device interface 1018 that can be coupled to system bus 1008, but can be connected by other interfaces, such as a parallel port, an IEEE serial port, a game port and/or a universal serial bus (USB) port.

Computer 1002 can operate in a networked environment using logical connections via wired and/or wireless communications to one or more remote computers, such as remote computer(s) 1032. Remote computer(s) 1032 can be a workstation, a server computer, a router, a personal computer, portable computer, microprocessor-based entertainment appliance, a peer device or other common network node, and typically includes many or all of the elements described relative to computer 1002, although, for purposes of brevity, only memory/storage device 1034 is illustrated. The logical connections depicted include wired/wireless connectivity to a local area network (LAN) 1026 and/or larger networks, e.g., WAN 1024, as well as smaller PANs involving a few devices (e.g., at least two). LAN and WAN networking environments are commonplace in the home, offices (e.g., medical facility offices, hospital offices) and companies, and facilitate enterprise-wide computer networks, such as intranets, all of which can connect to a global communications network (e.g., the Internet).

When used in a LAN networking environment, computer 1002 can be connected to local network through a wired and/or wireless communication network interface or adapter 1020. Adapter 1020 can facilitate wired or wireless communication to LAN 1026, which can also include a wireless access point (AP) connected to the LAN 1026 for communicating with adapter 1020.

When used in a WAN networking environment, computer 1002 can include modem 1022 or can be connected to a communications server on WAN 1024 or has other apparatus for establishing communications over WAN 1024, such as by way of the Internet. Modem 1022, which can be internal or external and a wired or wireless device, can be connected to system bus 1008 via input device interface 1018. In a networked environment, program modules depicted relative to computer 1002 or portions thereof, can be stored in a remote memory/storage device. It will be appreciated that the network connections shown are example and other apparatus of establishing a communications link between the computers can be used.

Computer 1002 can be operable to communicate with any wireless devices or entities operatively disposed in wireless communication via any number of protocols, including, but not limited to, NFC, Wi-Fi and/or BLUETOOTH® wireless protocols. Thus, the communication can be a defined structure as with a conventional network or simply an ad hoc communication between at least two devices.

NFC can allow point-to-point connection to an NFC-enabled device in the NFC field of an IMD within the home or at any location. NFC technology can be facilitated using an NFC-enabled smart phone, tablet or other device that can be brought within 3-4 centimeters of an implanted NFC component. NFC typically provides a maximum data rate of 424 kilobits per second (Kbps), although data rates can range from 6.67 Kbps to 828 Kbps. NFC typically operates at the frequency of 10.56 megahertz (MHz). NFC technology communication is typically over a range not exceeding 0.2 meters (m) and setup time can be less than 0.1 seconds. Low power (e.g., 10 milliamperes (mAs)) reading of data can be performed by an NFC device.

Wi-Fi can allow connection to the Internet from a couch at home, a bed in a hotel room or a conference room at work, without wires. Wi-Fi is a wireless technology similar to that used in a cell phone that enables such devices, e.g., computers, to send and receive data indoors and out. Wi-Fi networks use radio technologies called IEEE 802.11 (a, b, g, n, etc.) to provide secure, reliable, fast wireless connectivity. A Wi-Fi network can be used to connect computers to each other, to the Internet, and to wired networks (which can use IEEE 802.3 or Ethernet). Wi-Fi networks operate in the unlicensed 2.4 and 5 GHz radio bands, at an 11 Mbps (802.11a) or 54 Mbps (802.11b) data rate, for example or with products that contain both bands (dual band), so the networks can provide real-world performance similar to the basic 10BaseT wired Ethernet networks used in many offices.

The embodiments of devices described herein can employ artificial intelligence (AI) to facilitate automating one or more features described herein. The embodiments (e.g., in connection with automatically identifying acquired cell sites that provide a maximum value/benefit after addition to an existing communication network) can employ various AI-based schemes for carrying out one or more embodiments thereof. Moreover, the classifier can be employed to determine a ranking or priority of each cell site of an acquired network. A classifier is a function that maps an input attribute vector, x=(x1, x2, x3, x4, . . . , xn), to a confidence that the input belongs to a class, that is, f(x)=confidence (class). Such classification can employ a probabilistic and/or statistical-based analysis (e.g., factoring into the analysis utilities and costs) to prognose or infer an action that a mobile device desires to be automatically performed. A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated, one or more of the embodiments can employ classifiers that are explicitly trained (e.g., via a generic training data) as well as implicitly trained (e.g., via observing mobile device behavior, operator preferences, historical information, receiving extrinsic information). For example, SVMs can be configured via a learning or training phase within a classifier constructor and feature selection module. Thus, the classifier(s) can be used to automatically learn and perform a number of functions, including but not limited to determining according to a defined criteria which of the acquired cell sites will benefit a maximum number of subscribers and/or which of the acquired cell sites will add minimum value to the existing communication network coverage, etc.

As employed herein, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components or any combination thereof designed to perform the functions described herein. Processors can exploit nano-scale architectures such as, but not limited to, molecular and quantum-dot based transistors, switches and gates, in order to optimize space usage or enhance performance of mobile device equipment. A processor can also be implemented as a combination of computing processing units.

Memory disclosed herein can include volatile memory or nonvolatile memory or can include both volatile and nonvolatile memory. By way of illustration, and not limitation, nonvolatile memory can include ROM, programmable ROM (PROM), electrically programmable ROM (EPROM), electrically erasable PROM (EEPROM) or flash memory. Volatile memory can include RAM, which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The memory (e.g., data storages, databases) of the embodiments is intended to include, without being limited to, these and any other suitable types of memory.

As used herein, terms such as "data storage," "database," and substantially any other information storage component relevant to operation and functionality of a component, refer to "memory components," or entities embodied in a "memory" or components including the memory. It will be appreciated that the memory components or computer-readable storage media, described herein can be either volatile memory or nonvolatile memory or can include both volatile and nonvolatile memory.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word "example" or "exemplary" is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application should generally be construed to mean "one or more" unless specified otherwise or clear from context to be directed to a singular form. The terms "first," "second," "third," and so forth, as used in the claims and description, unless otherwise clear by context, is for clarity only and doesn't necessarily indicate or imply any order in time.

What has been described above includes mere examples of one or more embodiments. It is, of course, not possible to describe every conceivable combination of components or methodologies for purposes of describing these examples, but one of ordinary skill in the art can recognize that many further combinations and permutations of the present embodiments are possible. Accordingly, the embodiments disclosed and/or claimed herein are intended to embrace all such alterations, modifications and variations that fall within the spirit and scope of the detailed description and the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An implantable medical device configured to be at least partially implanted within a patient, comprising:
   a housing configured to be implanted at least partially within the patient;

a memory, within the housing, that stores executable components; and circuitry, within the housing, and configured to at least one of obtain information regarding a sensed physiological characteristic associated with the patient or deliver a therapy to the patient;

a processor, within the housing, that executes the executable components stored in the memory, wherein the executable components comprise:

a communication component configured to receive a communication request from an external device via a telemetry communication link established between the implantable medical device and the external device, wherein the communication request comprises a request for data from the implantable medical device; and a throughput monitoring component configured to monitor uplink throughput associated with transmission of the data by the implantable medical device to the external device via the telemetry communication link, wherein the communication component is further configured to terminate the telemetry communication link based on the uplink throughput being below a threshold value, wherein monitoring uplink throughput comprises determining a rate of successful message delivery associated with the transmission of the data, wherein the threshold value varies based on a type of telemetry session associated with the communication request.

2. The implantable medical device of claim 1, wherein the throughput monitoring component is configured to determine the uplink throughput based on a number of application data packets comprising the data that are transmitted by the implantable medical device to the external device via the telemetry communication link per connection interval.

3. The implantable medical device of claim 1, wherein the throughput monitoring component is configured to determine the uplink throughput based on time delays between successful transmissions of data packets comprising the data by the implantable medical device to the external device via the telemetry communication link.

4. The implantable medical device of claim 1, wherein the data comprises a first type of data and wherein the uplink throughput comprises first uplink throughput, and wherein the throughput monitoring component is configured to monitor the first uplink throughput independently from second uplink throughput associated with transmission of a second type of data by the implantable medical device to the external device via the telemetry communication link, wherein the second uplink throughput comprises a second rate of successful message delivery associated with the transmission of the second type of data.

5. The implantable medical device of claim 1, wherein the communication component is further configured to terminate the telemetry communication link based on the uplink throughput being below the threshold value for a defined period of time following reception of the communication request.

6. The implantable medical device of claim 5, wherein the defined period of time varies based on a type of telemetry session associated with the communication request.

7. The implantable medical device of claim 1, wherein the transmission of the data comprises transmission of one or more data packets comprising the data, and wherein the throughput monitoring component is configured to determine the uplink throughput based on whether the communication component receives one or more acknowledgment messages from the external device that indicate the external device received the one or more data packets.

8. The implantable medical device of claim 1, wherein the transmission of the data comprises transmission of one or more data packets comprising the data, and wherein the throughput monitoring component is configured to determine the uplink throughput based on timing of reception, by the communication component, of one or more acknowledgment messages from the external device that indicate the external device received the one or more data packets.

9. A device, comprising:

a memory that stores executable components; and a processor that executes the executable components stored in the memory, wherein the executable components comprise:

a communication component configured to transmit data to an implantable medical device via a telemetry communication link established between the device and the implantable medical device; and a throughput monitoring component configured to monitor uplink throughput associated with transmission of the data by the device to the implantable medical device, wherein monitoring the first uplink throughput comprises determining a data rate associated with how quickly the data is transmitted, and wherein the communication component is further configured to terminate the telemetry communication link based on the uplink throughput being below a threshold value, and wherein the device is external to the implantable medical device, wherein the threshold value varies based on a type of the data.

10. The device of claim 9, wherein the throughput monitoring component is configured to determine the uplink throughput based on number of application data packets comprising the data that are successfully transmitted by the device per connection interval.

11. The device of claim 9, wherein the throughput monitoring component is configured to determine the uplink throughput based on time delays between successful transmissions of data packets comprising the data by the device.

12. The device of claim 9, wherein the communication component is further configured to terminate the telemetry communication link based on the uplink throughput being below the threshold value for a defined period of time following establishment of the telemetry communication link.

13. The device of claim 12, wherein the defined period of time varies based on a type of telemetry session associated with establishment of the telemetry communication link.

14. A method, comprising:

receiving, by an implantable medical device comprising a processor, a data request from an external device via a telemetry communication link established between the implantable medical device and the external device, wherein the data request comprises a request for data from the implantable medical device;

monitoring, by the implantable medical device, uplink throughput associated with transmission of the data by the implantable medical device to the external device via the telemetry communication link, wherein the monitoring uplink throughput comprises determining a rate of successful message delivery of the data; and terminating, by the implantable medical device, the telemetry communication link based on the uplink throughput being below a threshold value, wherein the threshold value varies based on a type of telemetry session associated with the communication request.

15. The method of claim 14, wherein the monitoring the uplink throughput comprises determining the uplink throughput based on number of application data packets comprising the data that are successfully transmitted by the implantable medical device per connection interval.

16. The method of claim 14, wherein the monitoring the uplink throughput comprises determining the uplink throughput based on time delays between successful transmissions of data packets comprising the data by the implantable medical device.

17. The method of claim 14, wherein the monitoring comprises monitoring the uplink throughput associated with the transmission of the data based on a type of the data.

18. The method of claim 14, wherein the terminating comprises terminating the telemetry communication link based on the uplink throughput being below the threshold value for a defined period of time following reception of the data request.

19. The method of claim 18, wherein the defined period of time varies based on a type of telemetry session associated with the data request.

20. A system, comprising:
an external device, and
an implantable medical device configured to be at least partially implanted within a patient, comprising:
a first memory that stores first executable components; and
a first processor that executes the first executable components stored in the first memory, wherein the first executable components comprise:
a first communication component configured to establish a secure telemetry connection with the external device based on reception of a connection request from the external device; and
a first throughput monitoring component configured to monitor first uplink throughput associated with transmission of first data by the implantable medical device to the external device via the secure telemetry connection, and wherein the first communication component is further configured to terminate the secure telemetry connection based on a first determination, by the first throughput monitoring component, that the first uplink throughput is below a threshold value, wherein monitoring the first uplink throughput comprises determining a data rate associated with how quickly the data is transmitted, and wherein the threshold value varies based on a type of telemetry session associated with the communication request.

21. The system of claim 20, wherein the first throughput monitoring component is configured to determine the first uplink throughput based on a number of application data packets comprising the first data that are successfully transmitted by the implantable medical device to the external device via the secure telemetry connection per connection interval.

22. The system of claim 20, wherein the first throughput monitoring component is configured to determine the first uplink throughput based on time delays between successful transmissions of data packets comprising the first data by the implantable medical device to the external device via the secure telemetry connection per connection interval.

23. The system of claim 20, wherein the first data comprises a first type of data and wherein, and wherein the first throughput monitoring component is configured to monitor the first uplink throughput independently from second uplink throughput associated with transmission of a second type of data by the implantable medical device to the external device via the secure telemetry connection.

24. The system of claim 20, wherein the external device comprises:
a second memory that stores second executable components; and
a second processor that executes the second executable components stored in the second memory, wherein the second executable components comprise:
a second throughput monitoring component configured to monitor second uplink throughput associated with transmission of second data by the external device to the implantable medical device via the secure telemetry connection; and
a second communication component configured to terminate the secure telemetry connection based on a second determination, by the second throughput monitoring component, that the second uplink throughput is below the threshold value.

25. An implantable medical device configured to be at least partially implanted within a patient, comprising:
a housing configured to be implanted at least partially within the patient;
a memory, within the housing, that stores executable components; and
circuitry, within the housing, and configured to at least one of obtain information regarding a sensed physiological characteristic associated with the patient or deliver a therapy to the patient;
a processor, within the housing, that executes the executable components stored in the memory, wherein the executable components comprise:
a communication component configured to receive a communication request from an external device via a telemetry communication link established between the implantable medical device and the external device, wherein the communication request comprises a request for data from the implantable medical device; and
a throughput monitoring component configured to monitor uplink throughput associated with transmission of the data by the implantable medical device to the external device via the telemetry communication link, wherein the communication component is further configured to terminate the telemetry communication link based on the uplink throughput being below a threshold value, wherein monitoring uplink throughput comprises determining a rate of successful message delivery associated with the transmission of the data, wherein the threshold value varies based on a type of the data.

26. A method, comprising:
receiving, by an implantable medical device comprising a processor, a data request from an external device via a telemetry communication link established between the implantable medical device and the external device, wherein the data request comprises a request for data from the implantable medical device;
monitoring, by the implantable medical device, uplink throughput associated with transmission of the data by the implantable medical device to the external device via the telemetry communication link, wherein the monitoring uplink throughput comprises determining a rate of successful message delivery of the data; and
terminating, by the implantable medical device, the telemetry communication link based on the uplink throughput being below a threshold value, wherein the threshold value varies based on a type of the data.

27. A system, comprising:

an external device, and an implantable medical device configured to be at least partially implanted within a patient, comprising:
- a first memory that stores first executable components; and
- a first processor that executes the first executable components stored in the first memory, wherein the first executable components comprise:
  - a first communication component configured to establish a secure telemetry connection with the external device based on reception of a connection request from the external device; and
  - a first throughput monitoring component configured to monitor first uplink throughput associated with transmission of first data by the implantable medical device to the external device via the secure telemetry connection, and wherein the first communication component is further configured to terminate the secure telemetry connection based on a first determination, by the first throughput monitoring component, that the first uplink throughput is below a threshold value, wherein monitoring the first uplink throughput comprises determining a data rate associated with how quickly the data is transmitted, and wherein the threshold value varies based on a type of the first data.

28. An implantable medical device configured to be at least partially implanted within a patient, comprising:
- a housing configured to be implanted at least partially within the patient;
- a memory, within the housing, that stores executable components; and
- circuitry, within the housing, and configured to at least one of obtain information regarding a sensed physiological characteristic associated with the patient or deliver a therapy to the patient;
- a processor, within the housing, that executes the executable components stored in the memory, wherein the executable components comprise:
  - a communication component configured to:
    - receive a communication request from an external device via a telemetry communication link established between the implantable medical device and the external device, wherein the communication request comprises a request for data from the implantable medical device; and
    - terminate the telemetry communication link based on the uplink throughput being below the threshold value for a defined period of time following reception of the communication request, wherein the defined period of time varies based on a type of telemetry session associated with the communication request; and
  - a throughput monitoring component configured to monitor uplink throughput associated with transmission of the data by the implantable medical device to the external device via the telemetry communication link, wherein the communication component is further configured to terminate the telemetry communication link based on the uplink throughput being below a threshold value, wherein monitoring uplink throughput comprises determining a rate of successful message delivery associated with the transmission of the data.

29. A method, comprising:

receiving, by an implantable medical device comprising a processor, a data request from an external device via a telemetry communication link established between the implantable medical device and the external device, wherein the data request comprises a request for data from the implantable medical device;

monitoring, by the implantable medical device, uplink throughput associated with transmission of the data by the implantable medical device to the external device via the telemetry communication link, wherein the monitoring uplink throughput comprises determining a rate of successful message delivery of the data; and terminating, by the implantable medical device, the telemetry communication link based on the uplink throughput being below a threshold value, wherein the terminating comprises terminating the telemetry communication link based on the uplink throughput being below the threshold value for a defined period of time following reception of the data request, and wherein the defined period of time varies based on a type of telemetry session associated with the data request.

* * * * *